US012577200B2

(12) United States Patent
Koehler et al.

(10) Patent No.: US 12,577,200 B2
(45) Date of Patent: Mar. 17, 2026

(54) HIGH-THROUGHPUT METHOD TO RAPIDLY ADD CHEMICAL MOIETIES TO A SMALL MOLECULE LIBRARY

(71) Applicants: Massachusetts Institute of Technology, Cambridge, MA (US); President and Fellows of Harvard College, Cambridge, MA (US)

(72) Inventors: Angela N. Koehler, Belmont, MA (US); Christina Woo, Cambridge, MA (US); Catherine Henry, Keswick, VA (US); Chia-Fu Chang, Cambridge, MA (US); Sebastian Pomplun, Cambridge, MA (US); Jasmin Kruell, Cambridge, MA (US); Brice Curtin, Cambridge, MA (US)

(73) Assignees: Massachusetts Institute of Technology, Cambridge, MA (US); President and Fellows of Harvard College, Cambridge, MA (US)

( * ) Notice: Subject to any disclaimer, the term of this patent is extended or adjusted under 35 U.S.C. 154(b) by 1283 days.

(21) Appl. No.: 17/373,475

(22) Filed: Jul. 12, 2021

(65) Prior Publication Data

US 2022/0089537 A1 Mar. 24, 2022

Related U.S. Application Data

(60) Provisional application No. 63/080,234, filed on Sep. 18, 2020.

(51) Int. Cl.

| | |
|---|---|
| ***C07D 203/04*** | (2006.01) |
| ***C40B 40/04*** | (2006.01) |
| ***C40B 50/00*** | (2006.01) |

(52) U.S. Cl.
CPC ............ *C07D 203/04* (2013.01); *C40B 40/04* (2013.01); *C40B 50/00* (2013.01)

(58) Field of Classification Search
CPC ........ C07D 203/04; C40B 40/04; C40B 50/00
(Continued)

(56) References Cited

U.S. PATENT DOCUMENTS

| | | | |
|---|---|---|---|
| 6,306,663 | B1 | 10/2001 | Kenten |
| 7,932,213 | B2 | 4/2011 | Park |

(Continued)

FOREIGN PATENT DOCUMENTS

| | | |
|---|---|---|
| WO | 2012068251 | 5/2012 |
| WO | 2012167223 | 12/2012 |

(Continued)

OTHER PUBLICATIONS

Akhlaghinia, "A New and Convenient Method of Generating Alkyl Isocyanates from Alcohols, Thiols and Trimethylsilyl Ethers Using Triphenylphosphine/2,3Dichloro5,6dicyanobenzoquinone/Bu4NOCN", Synthesis, 12:19551958 (2005).

(Continued)

*Primary Examiner* — Aaron A Priest
*Assistant Examiner* — Randi Lynn Beil
(74) *Attorney, Agent, or Firm* — Pabst Patent Group LLP

(57) ABSTRACT

Organic compounds for target identification, drug discovery, chemical library production, high-throughput screening, fluorophore conjugation, chemiluminescent compound conjugation, creation of proximity induced modulators (e.g., protein degraders)/chimeric molecules, or a combination thereof are described. The compounds can contain small molecule moieties for identification of their potential targets; an isocyanate, photoactivatable groups; chemical moieties for enrichment and detection of target-small molecule moiety interactions; proximity induced modulator element; fluo-
(Continued)

rophores; chemiluminescent groups; or combinations thereof.

9 Claims, 7 Drawing Sheets

(58) Field of Classification Search
USPC ........................................................... 506/15
See application file for complete search history.

(56) References Cited

U.S. PATENT DOCUMENTS

| | | | | |
|---|---|---|---|---|
| 11,535,597 B2 * | 12/2022 | Cravatt | ................ | C07D 317/46 |
| 2008/0153802 A1 | 6/2008 | Lessene | | |
| 2013/0261023 A1 | 10/2013 | Barnes | | |

FOREIGN PATENT DOCUMENTS

| | | |
|---|---|---|
| WO | 2016019391 | 3/2017 |
| WO | 2017075630 | 5/2017 |
| WO | 2017075631 | 5/2017 |
| WO | 2018067615 | 4/2018 |
| WO | 2018226828 | 12/2018 |

OTHER PUBLICATIONS

Amada, et al., "5(1,3Benzothiazol6yl)4(4methyl1,3thiazol2yl) 1 Himidazole derivatives as potent and selective transforming growth factorβ type I receptor inhibitors", Bioorg. Med. Chem., 20(24):71287138 (2012).
Ayalamata, et al., "Synthesis of 6bromo2arylindoles using 2iodobenzoic acid as precursor", Tetrahedron Lett., 52(29):37263728 (2011).
Banik, et al., "Lysosome Targeting Chimeras (LYTACs) for the Degradation of Secreted and Membrane Proteins", ChemRxiv. Cambridge: Cambridge Open Engage, 168 (2019).
Bhat, et al., "Tandem Carbenoid C—H Functionalization/Coniaene Cyclization of N_Propargyl Indoles Generates Pyrroloindoles under Cooperative Rh(II)/Zn(II) Catalysis", Org. Lett., 22:224- 229 (2020).
Buckley, et al., "HaloPROTACS: Use of Small Molecule PROTACs to Induce Degradation of Halo Tag Fusion Proteins", ACS Chem. Biol., 10(8): 18311837 (2015).
Costales, et al., "Smallmolecule targeted recruitment of a nuclease to cleave an oncogenic RNA in a mouse model of metastatic cancer", PNAS, 117(5):24062411 (2020).
Ding, et al., "Emerging New Concepts of Degrader Technologies", Trends Pharmacol. Sci., 41(7):464474 (2020).
Ettari, et al., "Optimization Strategy of Novel PeptideBased Michael Acceptors for the Treatment of Human African Trypanosomiasis", Journal of Medicinal Chemistry 62(23):1061710629 (2019).
Ganem, "Trifluoroacetic AnhydrideCatalyzed Oxidation of Isonitriles by DMSO: A Rapid, Convenient Synthesis of Isocyanates", Org. Lett., 13:25842585 (2011).
Hong, et al., "Purinylhydantoins. Facile Conversion of the Naturally Occurring N(Purin6ylcarbamoyl) Lamino Acids into 3Purin6ylhydantoins and 3Cyclohexyll(purin6ylcarbamoyl)hydantoins", Journal of Medicinal Chemistry, 18(1):7984 (1975).
International Search Report for PCT/US2021/041299 dated Oct. 15, 2021.
Jarvis, "Targeted protein degraders are redefining how small molecules look and act" Chemical & Engineering News, 96(8): 111 (2018).
Knölker Hansjoachim, "Isocyanates, Part 4. Convenient PhosgeneFree Method for the Synthesis and Derivatization of Enantiopure [alpha]Isocyanato Carboxylic Acid Esters", Synlett, 8:925928 (1997).
Lai, et al., "Induced protein degradation: an emerging drug discovery paradigm", Nat. Rev. Drug Discov., 16:101-114 (2017).
Miller, "NMethylimidazoleCatalyzed Synthesis of Carbamates from Hydroxamic Acids via the Lossen Rearrangement", Org. Lett., 15(3):602605 (2013).
Mosayebnia, et al., "Novel and Efficient Method for Solid Phase Synthesis of UreaContaining Peptides Targeting Prostate Specific Membrane Antigen (PSMA) in Comparison with Current Methods", Iranian Journal of Pharmaceutical Research, 71(3):917926 (2018).
Petrilli, et al., "From Screening to Targeted Degradation: Strategies for the Discovery and Optimization of Small Molecule Ligands for PCSK9", Cell Chem. Biol., 27(1):3240e (2020).
Ravasco, "Bioconjugation with Maleimides: A Useful Tool for Chemical Biology Chemistry", Eur. J, 25:4359 (2019).
Roy, et al., "DUPA Conjugation of a Cytotoxic Indenoisoquinoline Topoisomerase I Inhibitor for Selective Prostate Cancer Cell Targeting", Journal of Medicinal Chemistry, 58(7):30943103 (2015).
Sandmann, et al., "Design and application of functional polymers: From selfhealing materials via hard tissue composites to methacrylate tougheners", Journal of Polymer Science, Part A: Polymer Chemistry, 52:239-247 (2014).
Sigmaaldrich, "ChemFiles: Resins for SolidPhase Peptide Synthesis", 3(4):132 (2003).
Siriwardena, et al., "PhosphorylationInducing Chimeric Small Molecules", J. Am. Chem. Soc., 142(33):1405214057(2020).
Smith, et al., "Targeted Intracellular Protein Degradation Induced by a Small Molecule: En Route to Chemical Proteomics", Bioorg. Med. Chem. Lett., 18(2):59045908 (2008).
Sterling, et al., "ZINC 15—Ligand Discovery for Everyone", J. Chem. Inf. Model., 55(11):23242337 (2015).
Takahashi, et al., "AUTACs: CargoSpecific Degraders Using Selective Autophagy", Molecular Cell, 76(5):797810 (2019).
Tan, et al., "Stereoselective Synthesis of over Two Million Compounds Having Structural Features Both Reminiscent of Natural Products and Compatible with Miniaturized CellBased Assays", J. Am. Chem. Soc., 120(33):85658566 (1998).
Uttamapinant, et al., "Fast, Cellcompatible Click Chemistry with Copperchelating Azides for Biomolecular Labeling", Angew. Chem. Int. Ed., 51(24):58525856 (2012).
Wang, et al., "Degradation of proteins by PROTACs and other strategies", Acta Pharmaceutica Sinica B, 10(2):207238 (2020).
Yamazoe, et al., "Heterobifunctional molecules induce dephosphorylation of kinases—a proof of concept study", J. Med. Chem., 63:28072813 (2020).
Yang, et al., "A bifunctional amino acid to study proteinprotein interactions", 10(69): 4207642083 (2020).
De Souza, et al., "Discovery of Potent, Reversible, and Competitive Cruzain Inhibitors with Trypanocidal Activity: A Structure-Based Drug Design Approach", Journal of Chemical Information and Modeling, vol. 60, No. 2, Feb. 24, 2020, pp. 1028-1041.

* cited by examiner 3a, 4a, 5a, and 6a: linker = $-(CH_2)_2-$ 2b, 3b, 4b, 5b, and 6b: linker = chemical group X = NR', O, S; R, R' = chemical group

Z obtained from

VHL Ligand 1 pomalidomide thalidomide lenalidomide

HIGH-THROUGHPUT METHOD TO RAPIDLY ADD CHEMICAL MOIETIES TO A SMALL MOLECULE LIBRARY

CROSS REFERENCE TO RELATED APPLICATIONS

This application claims the benefit of and priority to U.S. Provisional Application No. 63/080,234 filed Sep. 18, 2020, which is hereby incorporated herein by reference in its entirety.

STATEMENT REGARDING FEDERALLY SPONSORED RESEARCH

This invention was made with government support under grant number P30-CA14051 awarded by the National Cancer Institute, U54 Project Number 5U54CA143874-05 awarded by the National Cancer Institute, and NSF Career Award 1845464 awarded by the National Science Foundation. The U.S. government has certain rights in this invention.

FIELD OF THE INVENTION

The disclosed methods and compositions are generally in the field of chemical biology, and specifically in the area of detecting and investigating small molecule interactions in high-throughput screening.

BACKGROUND OF THE INVENTION

Many methods used to study small molecule-receptor (e.g., protein) interactions require the addition of chemical handles to small molecules to facilitate detection and/or enrichment of the small molecule-receptor (e.g., protein) interactions. However, there are no methods that facilitate the rapid modification of a small molecule library (e.g., drug-like small molecule library) with a desired chemical moiety. Currently the technology does not exist to quickly make chemical modifications to small molecules and to complete a rigorous identification of targets of these small molecules in a high-throughput pipeline, such as in drug-discovery. Further, compounds generated by adding a desired chemical moiety to small molecules in an unbiased way for high-throughput screening are not common. These problems exist in the field, because chemical modification of small molecules requires extensive experiments and modifications by a skilled chemist, and is extremely low-throughput. Accordingly, a need exists in the field for compounds, compositions, and methods that achieve this goal.

Therefore, it is an object of the invention to develop small molecules that are chemically modified, preferably once, when the small molecules have multiple potential locations that can be modified.

It is also an object of the invention to develop improved methods for the addition of chemical moieties to small molecules preferably once, when the small molecules have multiple potential locations that can be modified, for rapid synthesis and screening.

SUMMARY OF THE INVENTION

Compounds for receptor identification, drug discovery, chemical library production, high-throughput screening, fluorophore conjugation, conjugation of chemiluminescent compounds, conjugation of proximity induced modulator elements, or a combination thereof, have been developed. The compounds can contain small molecule moieties for identification of their potential targets; isocyanate groups; photoactivatable groups; chemical moieties for enrichment and detection of target-small molecule moiety interactions; proximity induced modulator elements; fluorophores; chemiluminescent compounds; or combinations thereof.

The compounds have the general formula:

Formula I

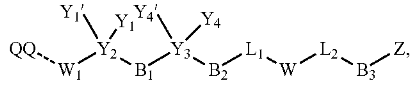

wherein Z is a small molecule between 50 Da and 2,500 Da, inclusive. Preferably, Z is not an amino acid. The dashed line between QQ and W1 denotes the presence or absence of a bond. When QQ is absent, preferably W1 contains —C(O)OH or —C(O)$NR_2R_3$ or —$NR_2$C(O)$R_3$, where $R_2$ and $R_3$ are preferably independently hydrogen, unsubstituted alkyl, or substituted alkyl. When QQ is present, preferably, QQ is a trityl chloride resin or Sieber amide resin containing a polystyrene bead, W1 contains —OC(O)—, —C(O)O—, —C(O)$NR_2$—, where $R_2$ is preferably hydrogen, unsubstituted alkyl, or substituted alkyl, more preferably hydrogen. B1 is absent and W is —NHC(O)X—, X is O, S, or NR', and R' is hydrogen. Further, in some forms:

(i) Y2 is substituted C1 alkyl; Y1' is hydrogen; Y1 is a substituted amide or a substituted alkyl, wherein the substituted amide or substituted alkyl contains a photoactivatable group (such as a diazirine) and/or an alkyne; and Y3, Y4, Y4', B2, B3, L1, and L2 are absent;

(ii) Y2 is substituted C1 alkyl; Y1' is hydrogen; Y1 is a substituted alkyl containing a photoactivatable group (such as a diazirine) and/or an alkyne; Y3, Y4, Y4', L2, and B3 are absent; B2 is —NHC(O)—; and L1 is —$(CH_2)_2$;

(iii) Y2 is substituted C1 alkyl; Y1' is hydrogen; Y1 is a substituted alkyl containing substituted alkyl or substituted amide containing a naphthyl group (e.g., 2-naphthyl) or a fluorophore such as a dansyl group; Y3, Y4, Y4', L2, and B3 are absent; B2 is —NHC(O)—; and L1 is —$(CH_2)_2$;

(iv) Y2 is substituted C1 alkyl; Y1' is hydrogen; Y1 is a substituted amide containing a fluorophore or chemiluminescent compound; Y3 is C1 unsubstituted alkylene; Y4 and Y4' are hydrogen; L1, L2, B2, and B3 are absent;

(v) Y2 is a fluorophore or chemiluminescent compound; Y3, Y4, Y4', L2, and B3 are absent; B2 is —NHC(O)—; and L1 is —$(CH_2)_2$—;

(vi) Y2 is substituted C1 alkyl; Y1 and Y1' are hydrogen; Y3 is substituted C1 alkyl; Y4' is hydrogen; Y4 is substituted alkyl containing an amide and a proximity induced modulator element, or Y4 is a substituted amide containing a proximity induced modulator element; B2 is —NHC(O)—; L1 is an organic chemical group such as substituted $C_1$-$C_{10}$ alkyl, substituted $C_1$-$C_{10}$ alkylene, unsubstituted $C_1$-$C_{10}$ alkylene, substituted $C_2$-$C_{10}$ alkenyl, substituted $C_2$-$C_{10}$ alkynyl, $C_1$-$C_{10}$ substituted heteroalkyl, substituted aryl, substituted heteroaryl, substituted $C_1$-$C_{10}$ alkoxy, substituted aroxy, substituted $C_1$-$C_{10}$ alkylthio, substituted arylthio, substituted $C_1$-$C_{10}$ carbonyl, substituted $C_1$-$C_{10}$ carboxyl, substituted $C_1$-$C_{10}$ amino, substituted $C_1$-$C_{10}$ amido, substituted $C_1$-$C_{10}$ sulfonyl, substituted $C_1$-$C_{10}$ sulfamoyl, substituted $C_1$-$C_{10}$ phosphonyl, substituted polyaryl, substituted $C_3$-$C_{20}$ cyclyl, or substituted heterocyclyl; and L2 and B3 are absent; or (vii) W is —NHC(O)X—, wherein X is NR'— and X together with Z form a substituted heterocyclyl (such as 4-(dimethylamino)piperidine) or unsubstituted heterocyclyl (such as piperidine), wherein a nitrogen in X is covalently bonded to the carbon in W; and L2 and B3 are absent.

Also provided are generalized, high-throughput methods to add chemical moieties to small molecules to generate these compounds in an unbiased way, i.e., the modification occurs preferably once, when the small molecules have multiple potential functional groups that can be modified. The chemically modified small molecules can be used to generate drug-like chemical libraries.

DETAILED DESCRIPTION OF THE INVENTION

I. Definitions

Figure 1:
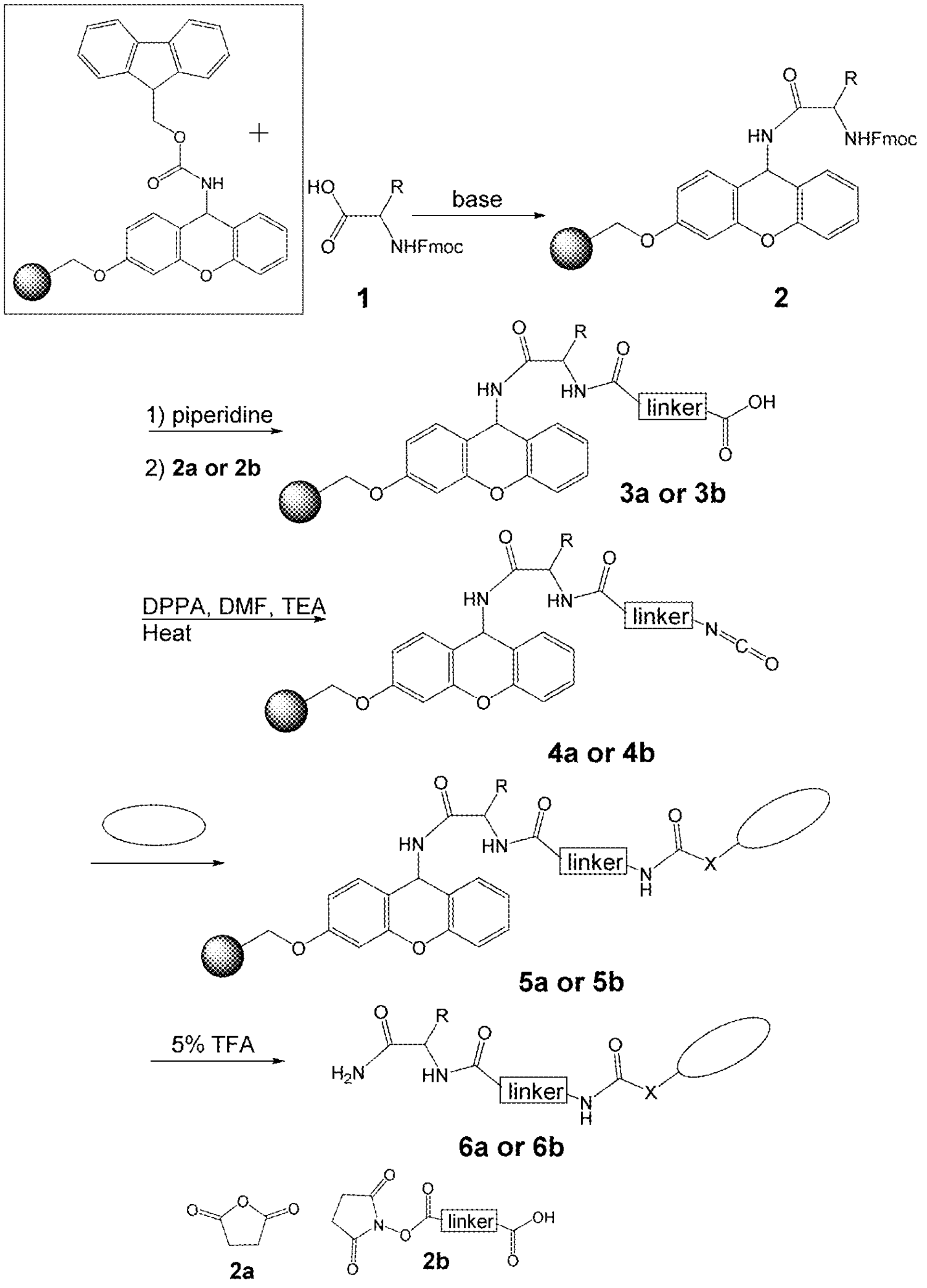
FIG. 1 is a schematic reaction showing how to modify a small molecule or small molecules in chemical libraries. The oval denotes a small molecule. The structures or moieties in the rectangle denote a resin prior to and after attachment of a chemical compound. The resin is a Sieber amide resin with the circle containing polystyrene. The resin can also be any of the other resins listed below.

"Photoactivatable group" refers to an organic chemical group that forms a highly reactive intermediate (such as carbene radicals, nitrene radicals, ketyl radicals, or nitrilimines) upon irradiation with an energy source, such as light. The light can be UV light.

"Proximity induced modulator" refers to bifunctional molecules that contain a receptor binding element and an element (called herein a proximity induced modulator element) that binds to a molecule that alters the activity of the receptor through proximity mediated effects, such as degradation and post-translational modifications. Typically, one or more molecules are recruited that bind to the receptor or chemically modify the receptor, thereby altering the activity of the receptor. In the case of proteins, for example, the bifunctional molecule contains a protein (e.g., protein receptor) binding element and a ubiquitination recognition element (that mediates its binding to another protein, such as E3 ubiquitin ligase). The protein binding element binds to a protein (e.g., receptor protein) and brings the protein (e.g., receptor protein) into close proximity of an E3 ubiquitin ligase through binding to the ubiquitination recognition element. The close proximity results in the ubiquitination of the protein (e.g., receptor protein) and subsequent degradation of the receptor protein by a proteasome.

"Chimeric compounds" refer to compounds that contain portions that are based on two or more different compounds. For illustrative purposes only, a chimeric molecule can contain (i) a fluorophore or chemiluminescent compound and a small molecule that binds to a receptor, (ii) a small molecule that binds to a receptor and an alkyne or biotin group, (iii) a small molecule that binds to a receptor and a photoactivatable group, (iv) a small molecule that binds to a receptor, a photoactivatable group, and an alkyne or biotin group, or (v) a small molecule that binds to a receptor, a photoactivatable group, a fluorophore or chemiluminescent compound, and an alkyne or biotin group. Accordingly, a protein induced modulator can be considered an example of a chimeric compound.

"Resin" generally refers to a final prepared composition formed from solutions or liquids containing polymers and/or monomers in an uncured state. After casting the solutions or liquids in a mold or film, they are polymerized or cured and cooled (if necessary) resulting in a solid or semi-solid state as the final prepared composition in the forms of films or the shape of the mold. The polymerization or curing involves a setting time, exposure to an energy source, or both. The energy source can be heat or other radiation energy such as an electron beam, UV light, or visible light. Individual resins can be distinguished using parameters such as chemical composition, degree of cross-linking, particle size, particle size distribution, and the amount and type of functionalities for anchoring organic compounds or linker moieties.

"Small molecule," and related terms such as "small molecule moiety," refers to an organic molecule that is less than about 2500 Da in molecular weight, less than about 1500 Da, less than about 1000 Da, less than about 800 Da, or less than about 500 Da.

II. Compositions

Compounds, for use in investigating small molecule interactions (such as small molecule-receptor interactions), receptor identification, drug discovery, chemical library production, high-throughput screening, fluorophore conjugation, chemiluminescent compound conjugation, proximity induced modulator element conjugation, creation of proximity induced modulators (e.g., protein degraders), or a combination thereof are described. A combination can contain small molecule moieties for identification of their potential targets; an isocyanate, photoactivatable groups; chemical moieties for enrichment and detection of target-small molecule moiety interactions; proximity induced modulator elements; fluorophores; chemiluminescent groups; or combinations thereof. Compounds that contain two or more combinations of these features are considered chimeric compounds. Some combinations can include, but are not limited to: (i) small molecule moieties (such as Z in Formula I) for identification of their potential targets, a photoactivatable group, and a chemical moiety (such as an alkyne or biotin) for enrichment and detection of target-small molecule moiety interactions; (ii) proximity induced modulator elements and small molecule moieties (such as Z in Formula I) for identification of its potential targets; (iii) fluorophores or chemiluminescent groups and small molecule moieties (such as Z in Formula I) for identification of the small molecule's potential target; (iv) isocyanates and one or more molecules or chemical moieties selected from proximity induced modulator elements, fluorophores, chemiluminescent compounds, photoactivatable groups, chemical moieties (such as an alkyne or biotin) for enrichment and detection of target-small molecule moiety interactions, and combinations thereof; (v) small molecule moieties (such as Z in Formula I) for identification of their potential targets and an alkyne or biotin group; or (vi) small molecule moieties (such as Z in Formula I) for identification of their potential targets, a photoactivatable group, a fluorophore or chemiluminescent compound, and an alkyne or biotin.

A. Compounds

The compounds have the general formula:

Formula I

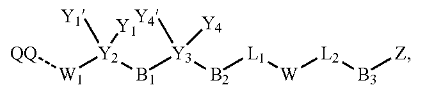

wherein Z is a small molecule moiety having a molecular weight less than 2,500 Da, between 50 Da and 2,500 Da, inclusive, or between 70 Da and 2,500 Da, inclusive, wherein W is —NHC(O)X—, a thiosuccinimide, a thiomaledimide, a hydrazone, an amidine, a thioamide, a phosphonamidate, an azo, a dialkyl dialkoxysilane, a diaryl dialkoxysilane, an orthoester, an acetal, an aconityl, a β-thiopropionate, a phosphoramidate, a trityl, a vinyl ether, a polyketal, or a combination thereof, X is O, NR', or S, preferably W is —NHC(O)X—, or W is —NHC(O)X—, wherein X is NR'— and X together with Z form a substituted heterocyclyl (such as 4-(dimethylamino)piperidine) or unsubstituted heterocyclyl (such as piperidine), wherein a nitrogen in X is covalently bonded to the carbon in W; and L2 and B3 are absent, wherein QQ is absent, one or more resins, or well plates, and the dashed line means a bond is present between QQ and W1, when QQ is present, wherein, when QQ is absent, W1 contains a carboxyl group (such as —C(O)OH), a carbonyl group (such as —C(O)$R_1$), an ester (such as —C(O)O$R_1$ or —OC(O)$R_1$), an amide (such as —C(O)N$R_2R_3$ or —N$R_2$C(O)$R_3$), a thioester (—C(O)S$R_4$ or —SC(O)$R_4$), a hydrazide (such as —C(O)NH$NH_2$), an amine, or a carbinol (such as —$CH_2$OH), preferably, W1 contains a carboxyl group (such as —C(O)OH) or amide (such as —C(O)N$R_2R_3$ or —N$R_2$C(O)$R_3$, where $R_2$ and $R_3$ are independently hydrogen, unsubstituted alkyl, or substituted alkyl, or $R_2$ and $R_3$ are hydrogen), wherein, when QQ is present, W1 contains —OC(O)—, —C(O)O—, —N$R_2$C(O)—, —N$R_2$—, —C(O)—, —C(O)S—, —SC(O)—, —NHNHC(O)—, —S—, —O—, or a combination thereof, wherein Y2 is unsubstituted alkylene, substituted alkyl, a fluorophore, substituted alkenyl, substituted alkynyl, substituted heteroalkyl, substituted aryl, substituted heteroaryl, substituted alkoxy, substituted aroxy, substituted alkylthio, substituted arylthio, substituted carbonyl, substituted carboxyl, substituted amino, substituted amido, substituted sulfonyl, substituted sulfamoyl, substituted phosphonyl, substituted polyaryl, substituted $C_3$-$C_{20}$ cyclyl, substituted heterocyclyl, preferably unsubstituted $C_1$-$C_3$ alkylene (preferably $C_1$ alkylene), substituted $C_1$-$C_3$ alkyl (preferably substituted $C_1$ alkyl), a fluorophore, a chemiluminescent compound, wherein Y1 and Y1' are, as valency permits, independently hydrogen, substituted alkyl, substituted amide, unsubstituted alkyl, unsubstituted alkenyl, substituted alkenyl, unsubstituted alkynyl, substituted alkynyl, unsubstituted heteroalkyl, substituted heteroalkyl, unsubstituted aryl, substituted aryl, unsubstituted heteroaryl, substituted heteroaryl, unsubstituted alkoxy, substituted alkoxy, unsubstituted aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, unsubstituted amino, substituted amino, unsubstituted amide, unsubstituted amido, substituted amido, unsubstituted sulfonyl, substituted sulfonyl, unsubstituted sulfamoyl, substituted sulfamoyl, unsubstituted phosphonyl, substituted phosphonyl, unsubstituted polyaryl, substituted polyaryl, unsubstituted $C_3$-$C_{20}$ cyclyl, substituted $C_3$-$C_{20}$ cyclyl, unsubstituted heterocyclyl, substituted heterocyclyl, peptide, preferably Y1 and Y1' are hydrogen, or Y1, Y1', or both, independently are substituted alkyl or substituted amide, independently containing a photoactivatable group (such as diazirines, aryl azides, o-hydroxyaryl azides, p-hydroxyarylazides, halogenated aryl azides (such as tetrafluoroaryl azide), azidomethylcoumarins, anthraquinones, diazo compounds, benzophenones, and psoralens), a fluorophore, chemiluminescent compound, thioether, alkynyl (such as aliphatic alkynyl, or cycloalkynyl such as dibenzocylooctynes), biotin, alkenyl, —$N_3$, tetrazine, maleimido, aziridinyl, —CN, —SH, acryloyl, acrylamido, —C(O)O$R_9$, —C(O)$R_{10}$, vinyl sulfonyl, —OH, cyanate, thiocyanate, isocyanate, isothiocyanate, alkoxysilane, vinyl silane, silicon hydride, —N$R_{11}R_{12}$, acetohydrazide, acyl azide, acyl halide, N-hydroxysuccinimide ester, sulfonyl chloride, glyoxyloyl, oxiranyl, carbodiimide, aryl halide, imido ester), or a combination thereof (such as photoactivatable group and alkynyl; thioether, photoactivatable group, and alkynyl), wherein Y1, Y1', or both, optionally and independently contain a small molecule moiety, proximity induced modulator element, or both, wherein Y3 is absent, unsubstituted alkylene, substituted alkyl, a fluorophore, chemiluminescent compound, substituted alkenyl, substituted alkynyl, substituted heteroalkyl, substituted aryl, substituted heteroaryl, substituted alkoxy, substituted aroxy, substituted alkylthio, substituted arylthio, substituted carbonyl, substituted carboxyl, substituted amino, substituted amido, substituted sulfonyl, substituted sulfamoyl, substituted phosphonyl, substituted polyaryl, substituted $C_3$-$C_{20}$ cyclyl, substituted heterocyclyl, preferably is absent, unsubstituted $C_1$-$C_3$ alkylene (preferably $C_1$ alkylene), or substituted $C_1$-$C_3$ alkyl (preferably substituted $C_1$ alkyl), wherein Y4 and Y4' are, as valency permits, independently hydrogen, substituted alkyl, substituted amide, unsubstituted alkyl, unsubstituted alkenyl, substituted alkenyl, unsubstituted alkynyl, substituted alkynyl, unsubstituted heteroalkyl, substituted heteroalkyl, unsubstituted aryl, substituted aryl, unsubstituted heteroaryl, substituted heteroaryl, unsubstituted alkoxy, substituted alkoxy, unsubstituted aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, unsubstituted amino, substituted amino, unsubstituted amide, unsubstituted amido, substituted amido, unsubstituted sulfonyl, substituted sulfonyl, unsubstituted sulfamoyl, substituted sulfamoyl, unsubstituted phosphonyl, substituted phosphonyl, unsubstituted polyaryl, substituted polyaryl, unsubstituted $C_3$-$C_{20}$ cyclyl, substituted $C_3$-$C_{20}$ cyclyl, unsubstituted heterocyclyl, substituted heterocyclyl, peptide, preferably Y4 and Y4' are hydrogen, or Y4, Y4', or both, independently are substituted alkyl or substituted amide, optionally containing a photoactivatable group (such as diazirines, aryl azides, o-hydroxyaryl azides, p-hydroxyarylazides, halogenated aryl azides (such as tetrafluoroaryl azide), azidomethylcoumarins, anthraquinones, diazo compounds, benzophenones and psoralens), a fluorophore, chemiluminescent compound, thioether, alkynyl (such as aliphatic alkynyl, or cycloalkynyl such as dibenzocylooctynes), biotin, alkenyl, —$N_3$, tetrazine, maleimido, aziridinyl, —CN, —SH, acryloyl, acrylamido, —C(O)$OR_9$, —C(O)$R_{10}$, vinyl sulfonyl, —OH, cyanate, thiocyanate, isocyanate, isothiocyanate, alkoxysilane, vinyl silane, silicon hydride, —$NR_{11}R_{12}$, acetohydrazide, acyl azide, acyl halide, N-hydroxysuccinimide ester, sulfonyl chloride, glyoxyloyl, oxiranyl, carbodiimide, aryl halide, imido ester), optionally and independently a small molecule moiety, proximity induced modulator element, or a combination thereof (such as substituted alkyl, a substituted amide, and a small molecule moiety), wherein B1, B2, and B3 are independently absent, —$NR_{13}$C(O)— (such as —NHC(O)—), —O—, —S—, —$NR_{14}$—, amidine, thioamide, phosphonamidate, azo, dialkyl dialkoxysilane, diaryl dialkoxysilane, orthoester, acetal, aconityl, β-thiopropionate, phosphoramidate, trityl, vinyl ether, polyketal, or a combination thereof, preferably B1, B2, and B3 are independently absent, —$NR_{13}$C(O)— (such as —NHC(O)—), wherein L1 and L2 are independently absent, substituted $C_1$-$C_{10}$ alkyl, substituted $C_1$-$C_{10}$ alkylene, unsubstituted $C_1$-$C_{10}$ alkylene, substituted $C_2$-$C_{10}$ alkenyl, substituted $C_2$-$C_{10}$ alkynyl, $C_1$-$C_{10}$ substituted heteroalkyl, substituted aryl, substituted heteroaryl, substituted $C_1$-$C_{10}$ alkoxy, substituted aroxy, substituted $C_1$-$C_{10}$ alkylthio, substituted arylthio, substituted $C_1$-$C_{10}$ carbonyl, substituted $C_1$-$C_{10}$ carboxyl, substituted $C_1$-$C_{10}$ amino, substituted $C_1$-$C_{10}$ amido, substituted $C_1$-$C_{10}$ sulfonyl, substituted $C_1$-$C_{10}$ sulfamoyl, substituted $C_1$-$C_{10}$ phosphonyl, substituted polyaryl, substituted $C_3$-$C_{20}$ cyclyl, or substituted heterocyclyl, preferably having the structure Formula II

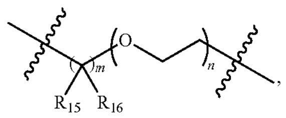

wherein m is an integer between 1 and 20, inclusive, (preferably between 1 and 10, inclusive, such as 1, 2, 3, 4, 5, 6, 7, 8, 9, or 10), n is an integer between 0 and 20, inclusive, (preferably between 1 and 10, such as 0, 1, 2, 3, 4, 5, 6, 7, 8, 9, or 10), wherein substituted means having one or more substituents selected from —OH, —SH, —$NO_2$, halogen, cyano, azido, oxo, $OR_{17}$, —C(O)$OR_{18}$, —OC(O)$R_{18}$, —C(O)$R_{19}$, —$NR_{20}R_{21}$, —$NR_{22}$C(O)$R_{23}$, —C(O)$NR_{22}R_{23}$, —$SR_{24}$, alkyl, alkenyl, aryl, heteroaryl, cycloalkyl, heterocyclyl, or a combination thereof, wherein R', $R_1$-$R_{24}$ are independently hydrogen, unsubstituted alkyl, substituted alkyl, unsubstituted alkenyl, substituted alkenyl, unsubstituted alkynyl, substituted alkynyl, unsubstituted heteroalkyl, substituted heteroalkyl, unsubstituted cycloalkyl, substituted cycloalkyl, unsubstituted heterocyclyl, substituted heterocyclyl, substituted aryl, unsubstituted aryl, substituted heteroaryl, unsubstituted heteroaryl, substituted hydroxyamino, or unsubstituted hydroxyamino, optionally, wherein (i) Z is not an amino acid residue, (ii) Z is not a lysine residue, (iii) Z is not an amino acid residue when W is —NHC(O)NH—, (iv) Z is not a lysine residue when W is —NHC(O)NH—, or (v) Formula I is not glutamate-urea-lysine.

In some forms, the compound is defined by Formula I, as described above, except that W is —NHC(O)X—, a thiosuccinimide, a thiomaledimide, a hydrazone, an amidine, a thioamide, a phosphonamidate, an azo, a dialkyl dialkoxysilane, or a diaryl dialkoxysilane. In some forms, the compound is defined by Formula I, as described above, except that W is —NHC(O)X—, a thiosuccinimide, or a thiomaledimide. In some forms, the compound is defined by Formula I, as described above, except that W is —NHC(O)X—. Examples of thiosuccinimides and thiomaleimides are described in Ravasco, et al., Chem. Eur. J. 2019, 25, 43-59, the contents of which are herein incorporated by reference in their entirety. In some forms, the compound is defined by Formula I, as described above, except that W is —NHC(O)X—, wherein X is NR'— and X together with Z form a substituted heterocyclyl (such as 4-(dimethylamino)piperidine) or unsubstituted heterocyclyl (such as piperidine), wherein a nitrogen in X is covalently bonded to the carbon in W; and L2 and B3 are absent.

In some forms, the compound is defined by Formula I, as described above, except that QQ is absent, and W1 contains —C(O)OH, —C(O)$R_1$, —C(O)$OR_1$, —OC(O)$R_1$, —C(O)$NR_2R_3$, —$NR_2$C(O)$R_3$, —C(O)$SR_4$, —SC(O)$R_4$, —C(O)

NHNH$_2$, or —CH$_2$OH. In some forms, the compound is defined by Formula I, as described above, except that QQ is absent and W1 contains —C(O)OH, —C(O)OR$_1$, —OC(O)R$_1$, —C(O)NR$_2$R$_3$, —NR$_2$C(O)R$_3$, —C(O)SR$_4$, or —SC(O)R$_4$. Preferably, in some forms, the compound is defined by Formula I, as described above, except that QQ is absent, and W1 contains —C(O)OH. However, W1 can depend on the type of covalent chemical attachment of a molecular moiety to the surface of a resin, and the conditions used to cleave the molecular moiety from the resin. Examples of resins and their cleavage conditions are described in ChemFiles: Resins for solid-phase peptide synthesis, Vol 3. No. 4 (downloaded Aug. 20, 2020), the contents of which are herein incorporated by reference in their entirety.

In some forms, the compound is defined by Formula I, as described above, except that Y2 is substituted $C_1$-$C_3$ alkyl or unsubstituted $C_1$-$C_3$ alkylene. In some forms, the compound is defined by Formula I, as described above, except that Y2 is substituted $C_1$ alkyl.

In some forms, the compound is defined by Formula I, as described above, except that Y1, Y1', Y4, and Y4' are independently hydrogen, substituted $C_1$-$C_{10}$ alkyl, substituted $C_1$-$C_{10}$ amide, unsubstituted $C_1$-$C_{10}$ alkyl, unsubstituted $C_2$-$C_{10}$ alkenyl, substituted $C_2$-$C_{10}$ alkenyl, unsubstituted $C_2$-$C_{10}$ alkynyl, substituted $C_2$-$C_{10}$ alkynyl, unsubstituted $C_1$-$C_{10}$ heteroalkyl, substituted $C_1$-$C_{10}$ heteroalkyl, unsubstituted aryl, substituted aryl, unsubstituted heteroaryl, substituted heteroaryl, unsubstituted $C_1$-$C_{10}$ alkoxy, substituted $C_1$-$C_{10}$ alkoxy, unsubstituted aroxy, substituted aroxy, unsubstituted $C_1$-$C_{10}$ alkylthio, substituted $C_1$-$C_{10}$ alkylthio, unsubstituted arylthio, substituted arylthio, unsubstituted $C_1$-$C_{10}$ carbonyl, substituted $C_1$-$C_{10}$ carbonyl, unsubstituted $C_1$-$C_{10}$ carboxyl, substituted $C_1$-$C_{10}$ carboxyl, unsubstituted $C_1$-$C_{10}$ amino, substituted $C_1$-$C_{10}$ amino, unsubstituted $C_1$-$C_{10}$ amide, unsubstituted $C_1$-$C_{10}$ amido, substituted $C_1$-$C_{10}$ amido, unsubstituted $C_1$-$C_{10}$ sulfonyl, substituted $C_1$-$C_{10}$ sulfonyl, unsubstituted $C_1$-$C_{10}$ sulfamoyl, substituted $C_1$-$C_{10}$ sulfamoyl, unsubstituted $C_1$-$C_{10}$ phosphonyl, substituted $C_1$-$C_{10}$ phosphonyl, unsubstituted polyaryl, substituted polyaryl, unsubstituted $C_3$-$C_{20}$ cyclyl, substituted $C_3$-$C_{20}$ cyclyl, unsubstituted heterocyclyl, substituted heterocyclyl, or peptide.

In some forms, the compound is defined by Formula I, as described above, except that, when present, Y1, Y1', Y4, or Y4', when present, independently contain a photoactivatable group, a fluorophore, chemiluminescent compound, thioether, alkynyl (such as aliphatic alkynyl, or cycloalkynyl such as dibenzocylooctynes), biotin, alkenyl, —N$_3$, tetrazine, maleimido, aziridinyl, —CN, —SH, acryloyl, acrylamido, —C(O)OR$_5$, —C(O)R$_6$, vinyl sulfonyl, —OH, cyanate, thiocyanate, isocyanate, isothiocyanate, alkoxysilane, vinyl silane, silicon hydride, —NR$_7$R$_8$, acetohydrazide, acyl azide, acyl halide, N-hydroxysuccinimide ester, sulfonyl chloride, glyoxyloyl, oxiranyl, carbodiimide, aryl halide, imido ester, or a combination thereof.

In some forms, the compound is defined by Formula I, as described above, except that Y1 is a substituted amide.

In some forms, the compound is defined by Formula I, as described above, except that Y1 is a substituted alkyl.

i. Photoaffinity Compounds

The compounds can contain one or more photoactivatable groups. When present, the photoactivatable groups are preferably in one or more of Y1, Y1', Y4, or Y4', as described above.

In some forms, the compound is defined by Formula I, as described above, except that Y1 contains between one and 10 carbon atoms, inclusive, between one and nine carbon atoms, inclusive, between one and eight carbon atoms, inclusive, between two and 10 carbon atoms, inclusive, between two and nine carbon atoms, inclusive, between two and eight carbon atoms, inclusive, between five and 10 carbon atoms, inclusive, between six and 10 carbon atoms, inclusive, or between seven and 10 carbon atoms, inclusive.

In some forms, the compound is defined by Formula I, as described above, except that Y1 contains an alkynyl.

In some forms, the compound is defined by Formula I, as described above, except that Y1' is hydrogen.

In some forms, the compound is defined by Formula I, as described above, except that Y1 contains a photoactivatable group. The photoactivatable group can be selected from diazirines, aryl azides, o-hydroxyaryl azides, p-hydroxyarylazides, halogenated aryl azides (such as tetrafluoroaryl azide), an α-ketoamide (such as a thienyl-substituted α-ketoamide), azidomethylcoumarins, anthraquinones, diazo compounds, psoralens, tetrazoles, benzophenones, or combinations thereof. In some forms, the photoactivatable group is diazirine.

In some forms, the compound is defined by Formula I, as described above, except that B1 is absent.

In some forms, the compound is defined by Formula I, as described above, except that B2, L1, and L2 are absent.

In some forms, the compound is defined by Formula I, as described above, except that the compounds have a structure:

Formula III

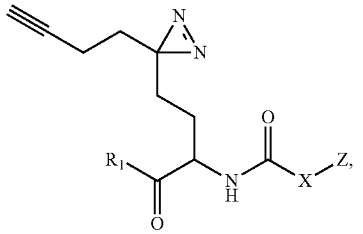

Formula IV

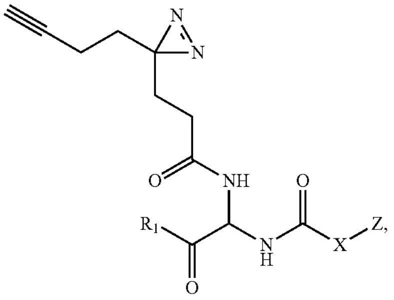

or

Formula V

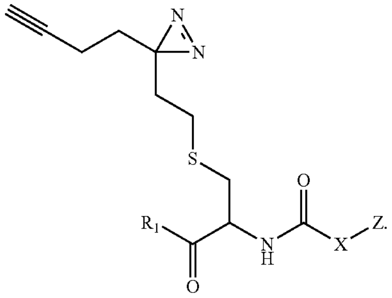

In some forms, the compound is defined by Formula I, as described above, except that B2 is —NHC(O)— and L1 is Formula II:

Formula II

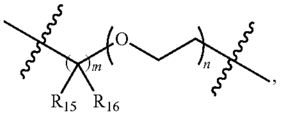

and $R_{15}$ and $R_{16}$ are hydrogen, m is 2, and n is 0.

In some forms, the compound is defined by Formula I, as described above, except that the compound has a structure:

Formula VI

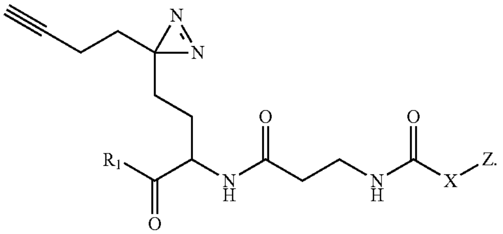

In some forms, the compound is defined by Formulae I, and III-VI, as described above, except that X is O, S, or NR'.

In some forms, the compound is defined by Formulae I, and III-VI, as described above, except that R' is hydrogen, unsubstituted alkyl, substituted alkyl, preferably hydrogen.

ii. Fluorophores

The compounds can contain one or more fluorophores or chemiluminescent compounds. When present, the fluorophores or chemiluminescent compounds are preferably in one or more of Y1, Y1', Y2, Y4, or Y4', as described above. In some forms, the compound is defined by Formula I, except that B2 is absent or —NHCO—, and L1 is absent or Formula II:

Formula II

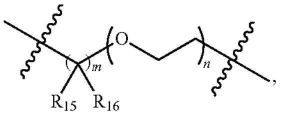

and $R_{15}$ and $R_{16}$ are hydrogen, m is 2, and n is 0.

In some forms, the compound is defined by Formula I, as described above, except that the compound has a structure:

Formula VII

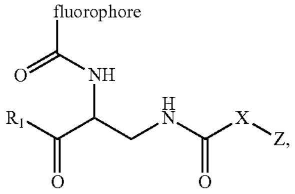

-continued

Formula VII'

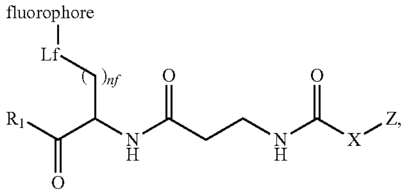
or

Formula VIII

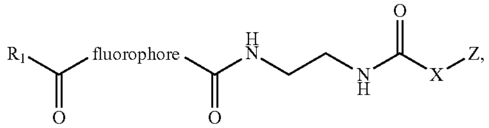

wherein of is an integer between 1 and 4, inclusive; and Lf is absent or —NH—, preferably, wherein $R_1$ is —OH or $NR_2R_3$, —$NR_2C(O)R_3$, wherein $R_2$ and $R_3$ independently hydrogen, unsubstituted alkyl, or substituted alkyl, preferably $R_2$ and $R_3$ are hydrogen.

In some forms, the compound is defined by Formulae I, VII, VII', and VIII, as described above, except that X is O, S, or NR'. In some forms, the compound is defined by Formula I, VII, VII', and VIII', as described above, except that W is —NHC(O)X—, wherein X is NR'— and X together with Z form a substituted heterocyclyl (such as 4-(dimethylamino)piperidine) or unsubstituted heterocyclyl (such as piperidine), wherein a nitrogen in X is covalently bonded to the carbon in W; and L2 and B3 are absent.

In some forms, the compound is defined by Formulae I, VII, VII', and VIII, as described above, except that R' is hydrogen, unsubstituted alkyl, substituted alkyl, preferably hydrogen.

In some forms, the compound is defined by Formulae I, VII, VII', and VIII, as described above, except that the fluorophore has a structure selected from:

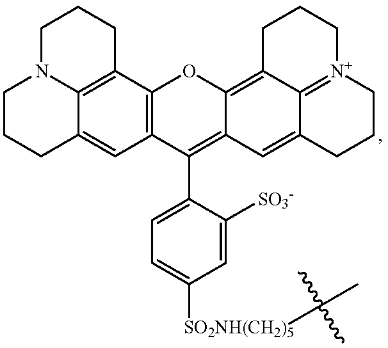

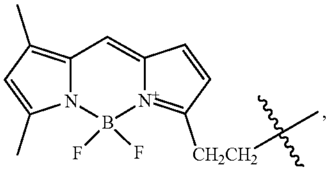

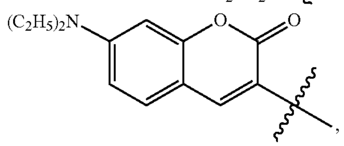

-continued
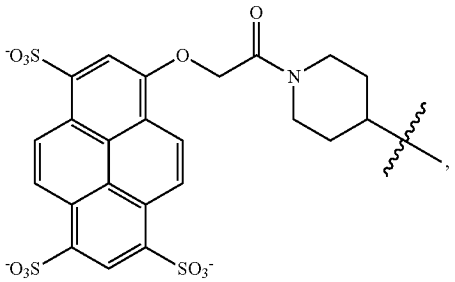
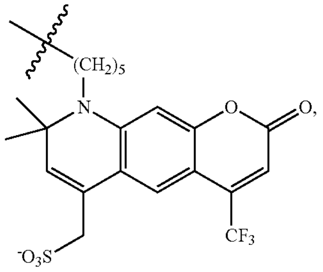
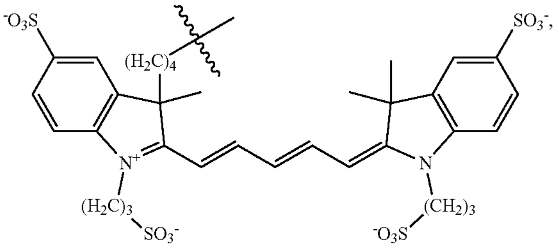
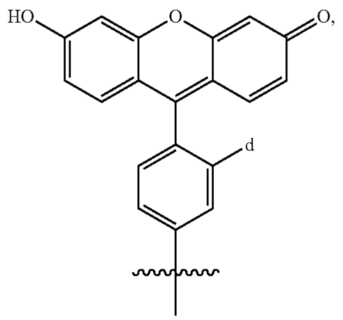
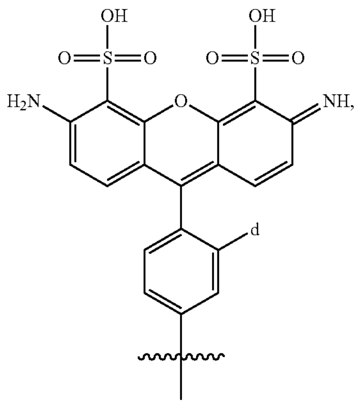
-continued
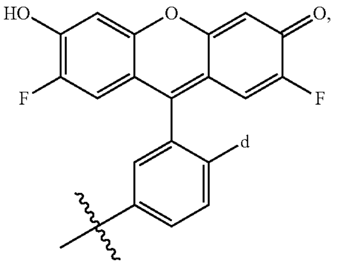
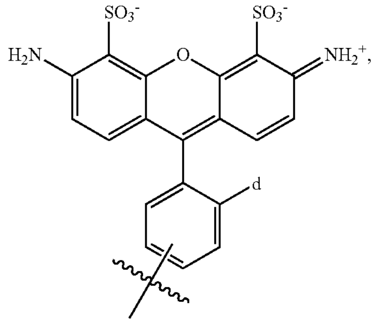
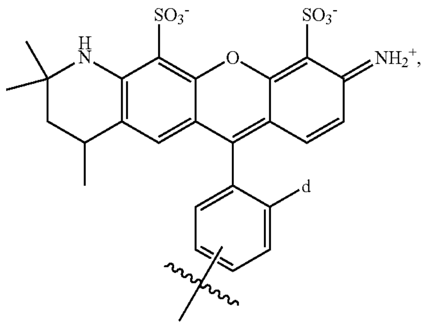
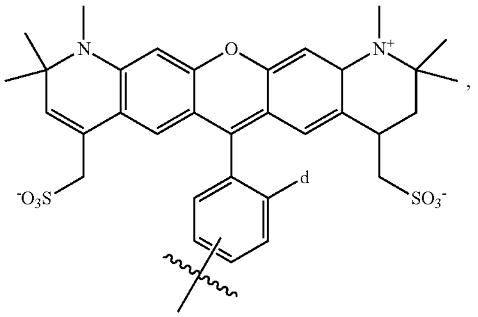
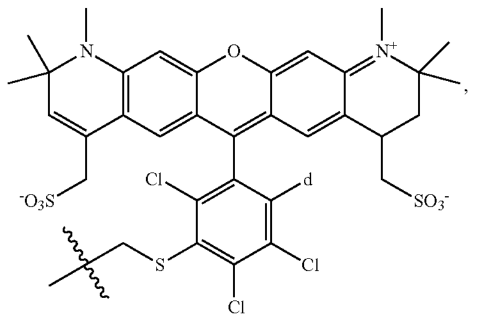

-continued

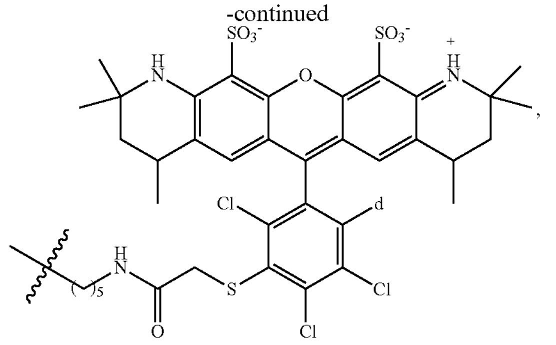

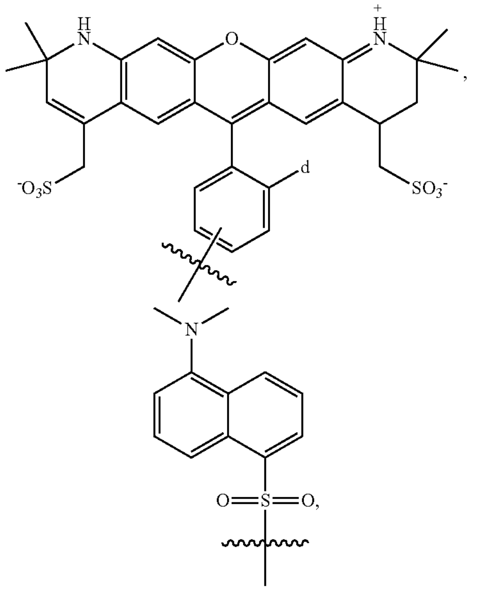

or a combination thereof, and wherein d is —C(O)$O^-$, —COOH.

iii. Proximity Induced Modulators

The compounds can be proximity induced modulators. When the compounds are proximity induced modulators, the compounds contain one or more proximity induced modulator elements. Proximity induced modulator elements include compounds that alter the activity of a receptor through proximity mediated effects. When present, the proximity induced modulator elements are preferably in one or more of Z, Y1, Y1', Y4, or Y4'. Proximity induced modulator elements are described in Smith, et al., Bioorg. Med. Chem. Lett. 2008, 18(2): 5904-5908; Buckley, et al., ACS Chem. Biol. 2015, 10(8): 1831-1837; Jarvis, Chemical and Engineering News, Feb. 19, 2018, 96(8); Wang, et al., Acta Pharmaceutica Sinica B 2020, 10(2), 207-238; Takahashi, et al., Molecular Cell 2019, 76(5), 797-810; Banik, et al., ChemRxiv Nov. 11, 2019; Lai and Crews, Nat. Rev. Drug Discov. 2017, 16(2), 101-114; and Ding, et al., Trends in Pharmacological Sciences 2020, 41(7), 464-474; Siriwardena, et al., J. Am. Chem. Soc., 2020, 142 (33), 14052-14057; Costales, et al., Proc. Natl. Acad. Sci. USA, 2020, 117(5), 2406-2411; Yamazoe, et al., J. Med. Chem., 2020, 63, 2807-2813; Petrilli, et al., Cell Chem. Biol., 2020, 27(1), 32-40e; the contents of which are herein incorporated by reference in their entirety.

In some forms, the compound is defined by Formula I, as described above, except that Y1, Y1', Y4, and Y4' independently contain a proximity induced modulator element.

In some forms, the compound is defined by Formula I, as described above, except that Y2 is unsubstituted $C_1$-$C_3$ alkylene.

In some forms, the compound is defined by Formula I, as described above, except that Y4 is a substituted alkyl, preferably containing a substituted amide, or Y4 is a substituted amide.

In some forms, the compound is defined by Formula I, as described above, except that Y4 contains the proximity induced modulator element.

In some forms, the compound is defined by Formula I, as described above, except that the compound has a structure:

Formula IX

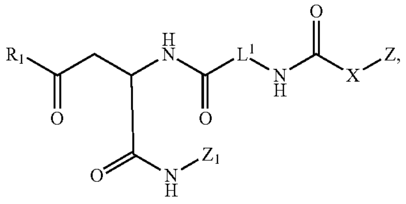

wherein Z1 is the proximity induced modulator element.

In some forms, the compound is defined by Formulae I and IX, as described above, except that the proximity induced modulator element is a VHL ligand (such as VHL ligand 1), a pomalidomide, a thalidomide, a lenalidomide, a foretinib, hydrophobic tag (such as Arg-Boc3 and adamantane), cGMP modification/S-guanylation degradation tag, glycopeptide ligand for CI-M6PR, autophagosome-tethering compound, bestatin esters, HaloTag, lysosomal-sorting signal peptide, RNF4 E3 ligase recruiter, deglycobelomycin, FKBP12 binders (such as SLF and FK506), CypA binders (such as cyclosporin A), a RIPK2, a dBET1, a SIRT2, cell inhibitor of apoptosis protein (cIAP) E3 ligase recruiter, RNase recruiter (such as 2'-5' poly(A) oligonucleotide), a MDM2 E3 ligase recruiter (such as nutlin 3-a, RG7112, and idasanutlin), beta-TrCP recruiter (such as a phosphopeptidic portion of IκBα), KEAP1 peptide for recruitment of Keapl-Cul3 ubiquitin E3 ligase, kinase recruiter (such as PF-0609577 and 9-(4-aminomethylbenzyloxy)-substituted benzolactam activator), phosphatase recruiter (such as PP1-disrupting-peptide-1), or a combination thereof.

iv. Small Molecules

The compounds contain one or more small molecule moieties. The small molecule moieties have a molecular weight less than 2,500 Da. In some forms, the small molecule moieties have a molecular weight between 50 Da and 2,500 Da, inclusive. In some forms, the small molecule moieties have a molecular weight between 70 Da and 2,500 Da, inclusive. In some forms, the small molecules are non-polymeric, and/or non-oligomeric. In some forms, the small molecules are polymeric, and/or oligomeric.

A small molecule moiety can be located, preferably, on one or more of Z, Y1, Y1', Y4, or Y4'. Preferably, the small molecule moiety contains one or more chemical moieties such as primary alcohols, secondary alcohols, phenols, primary amines, secondary amines, tertiary amines, anilines, thiols, hydroxyamines, carboxyls, or a combination thereof, for covalent attachment to the rest of the compound. In some forms, the small molecule moiety when present, is a therapeutic, diagnostic, or prophylactic agent.

The small molecules can be naturally occurring or non-naturally occurring. Examples of naturally occurring small molecules include taxol, dynemicin, and rapamycin. Examples of non-naturally occurring small molecules are those synthesized in a laboratory, and include compounds described in Tan, et al., J. Am. Chem. Soc. 1998, 120, 8565, the contents of which are herein incorporated by reference in their entire. Additional small molecules are described in the publicly available ZINC database of compounds (Sterling and Irwin, J. Chem. Inf. Model. 2015, 55 (11), 2324-2337).

Small molecules contemplated for inclusion to form small molecule moieties in the compounds can have known therapeutic functions, classified among the following categories: anticancer agents, analgesics/antipyretics, antidepressants, antibiotics, antidiabetics, antihypertensive agents, immunosuppressive agents, anti-inflammatories, antianxiety agents, antimigraine agents, sedatives/hypnotics, antianginal agents, antipsychotic agents, antiarrhythmics, antiarthritic agents, antigout agents, anticoagulants, antifibrinolytic agents, hemorheologic agents, antiplatelet agents, anticonvulsants, antihistamines, antibacterial agents, antiviral agents, antipruritics, antimicrobials, bronchodilators, steroidal compounds, hormones and hormone analogues, hypoglycemic agents, hypolipidemic agents, antiulcer/anti-reflux agents, antinauseants/antiemetics, oil-soluble vitamins, or a combination thereof.

These compounds and alternative forms of these compounds such as alternative salt forms, free acid forms, free base forms, and hydrates are contemplated.

v. Resins

The compounds can be immobilized on resins. Preferably, the resins are able to withstand temperature, solvent, concentration, and pH conditions involved in the synthesis of the compounds. An important feature involves further modification of the resin's surface to include a functional group such an isocyanate so that the small molecule moiety is integrated in a rapid and unbiased way, i.e., the modification occurs preferably once, when the small molecules have multiple potential locations that can be modified. For example, a small molecule than contains more than one nucleophile can be integrated onto the surface of the resin via any of the nucleophilic groups. Accordingly, several orientations of a single small molecule can be present for target identification purposes. Preferably, the functional group introduced on the surface of the resin are spatially separated, to prevent reactions between each other. In some forms the resins are loaded, such that between 1% and 80%, inclusive, 1% and 75%, inclusive, 1% and 70%, inclusive, 1% and 65%, inclusive, 1% and 60%, inclusive, 1% and 55%, inclusive, 1% and 50%, inclusive, 5% and 80%, inclusive, 10% and 80%, inclusive, 15% and 80%, inclusive, 20% and 80%, inclusive, 30% and 60%, inclusive, 50% and 60%, inclusive, 5%, 10%, 15%, 20%, 25%, 30%, 35%, 40%, 45%, 50%, 55%, 60%, 65%, 70%, or 75% of functional groups on their surfaces are modified. Further, immobilization on the surface of the resin facilitates the reaction of one functional group per small molecule. The spatial separation depends on the type of resin, type of small molecule to be modified, separation between the surface of the resin and the small molecule and/or solvent conditions. Preferably, the bond between the rest of the compound and the resin is more easily cleaved, compared to the bond between a small molecule moiety described above and the rest of the compound.

In some forms, the compound is defined by Formula I, as described above, except that QQ is present and a bond is present between QQ and W1.

In some forms, the compound is defined by Formula I, as described above, except that Z is isocyanate, a carboxyl, an amine, an isonitrile, an N-hydroxyacyl, a hydroxyl, a thiol, or a trialkylsilyl ether (such as trimethylsilyl ether).

In some forms, the compound is defined by Formula I, as described above, except that the compound has a structure:

Formula X

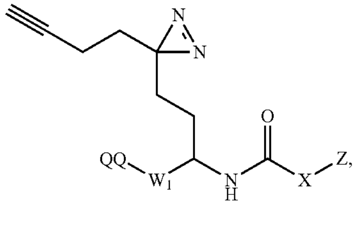

Formula XI

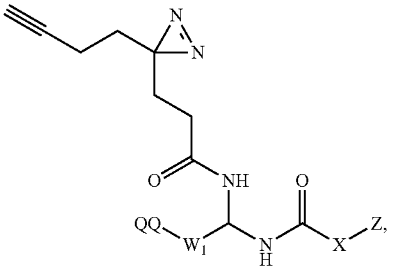

or

Formula XII

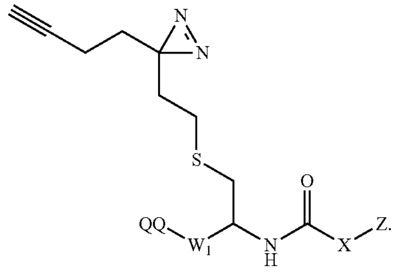

In some forms, the compound is defined by Formulae I and X-XII, as described above, except that B2 is —NHC(O)— and L1 is Formula II:

Formula II

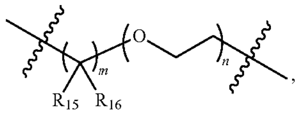

wherein $R_{15}$ and $R_{16}$ are hydrogen, m is 2, and n is 0.

In some forms, the compound is defined by Formula I, as described above, except that the compound has a structure:

Formula XIII

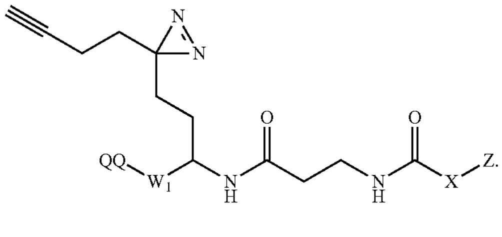

In some forms, the compound is defined by Formulae I, and X-XIII, as described above, except that X is O, S, or NR'. In some forms, the compound is defined by Formulae I, and X-XIII, as described above, except that W is —NHC(O)X—, wherein X is NR'— and X together with Z form a substituted heterocyclyl (such as 4-(dimethylamino)piperidine) or unsubstituted heterocyclyl (such as piperidine), wherein a nitrogen in X is covalently bonded to the carbon in W; and L2 and B3 are absent.

In some forms, the compound is defined by Formulae I, and X-XIII, as described above, except that R' is hydrogen, unsubstituted alkyl, substituted alkyl, preferably hydrogen.

Prior to cleavage from the resin, the compounds described herein, can contain one or more fluorophores or chemiluminescent compounds. When present, the fluorophores or chemiluminescent compounds are preferably in one or more of Y1, Y1', Y2, Y4, or Y4', as described above. In some forms, the compound is defined by Formula I, except that B2 is absent or —NHCO—, and L1 is absent or Formula II:

Formula II

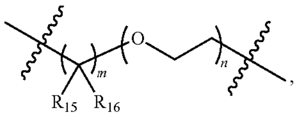

and $R_{15}$ and $R_{16}$ are hydrogen, m is 2, and n is 0.

In some forms, the compound is defined by Formula I, as described above, except that the compound has a structure:

Formula XIV

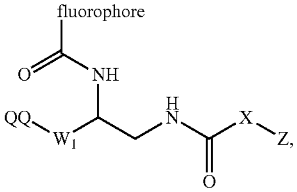

Formula XIV'

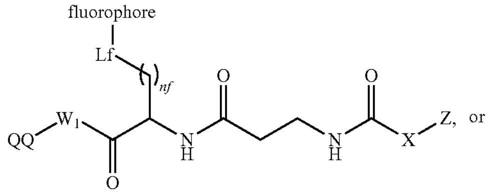

Formula XV

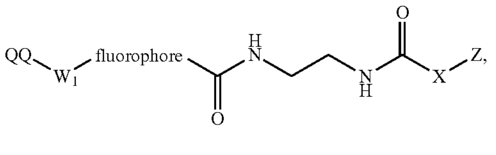

wherein of is an integer between 1 and 4, inclusive; and Lf is absent or —NH—.

In some forms, the compound is defined by Formulae I, XIV, XIV', and XV, as described above, except that X is O, S, or NR'. In some forms, the compound is defined by Formulae I, XIV, XIV', and XV, as described above, except that W is —NHC(O)X—, wherein X is NR'— and X together with Z form a substituted heterocyclyl (such as 4-(dimethylamino)piperidine) or unsubstituted heterocyclyl (such as piperidine), wherein a nitrogen in X is covalently bonded to the carbon in W; and L2 and B3 are absent.

In some forms, the compound is defined by Formulae I, XIV, XIV', and XV, as described above, except that R' is hydrogen, unsubstituted alkyl, substituted alkyl, preferably hydrogen.

In some forms, the compound is defined by Formulae I, XIV, XIV', and XV, as described above, except that the fluorophore has a structure selected from:

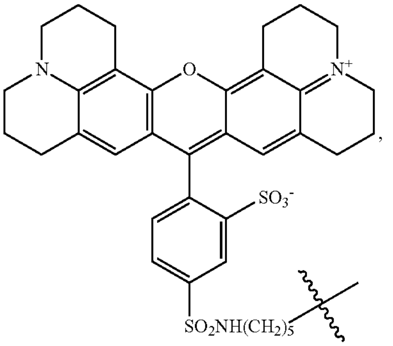

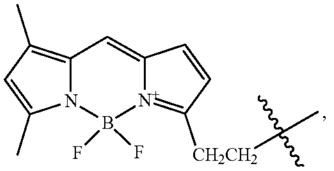

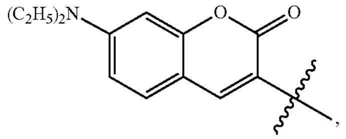

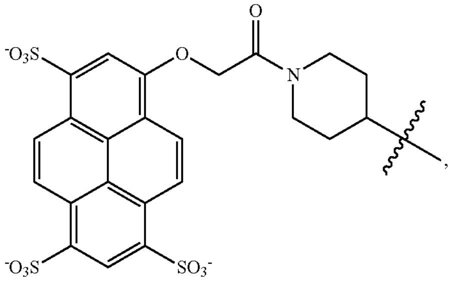

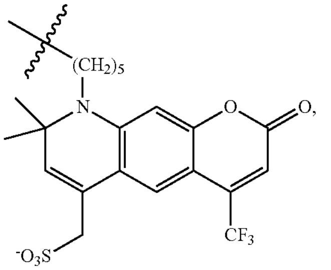

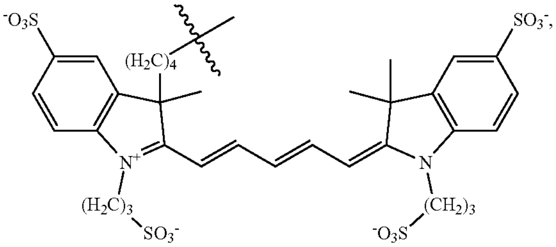

-continued
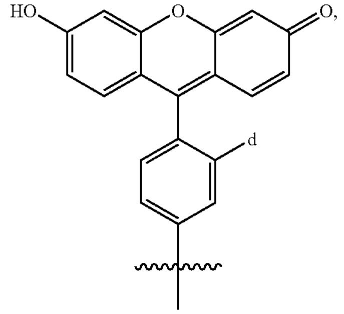
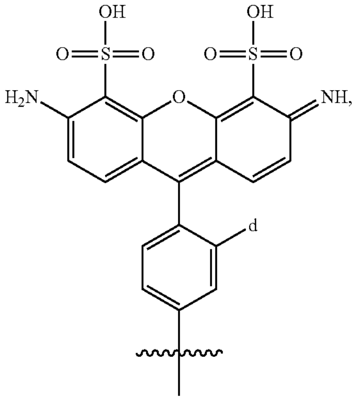
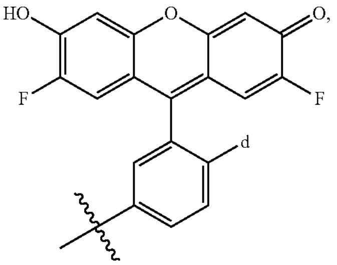
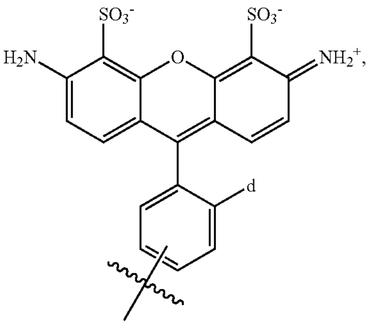
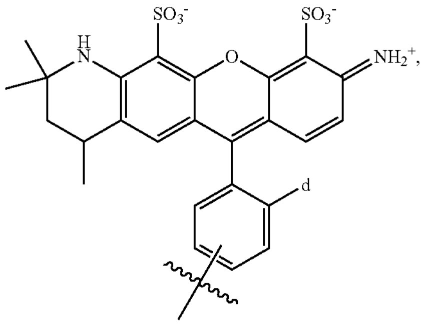
-continued
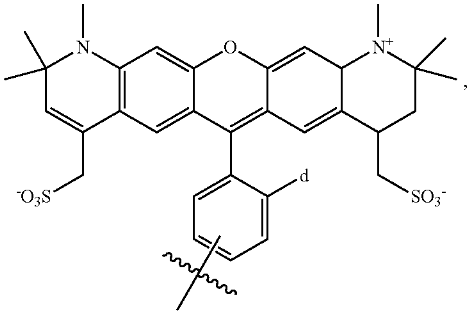
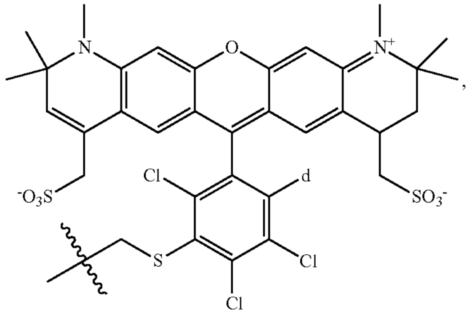
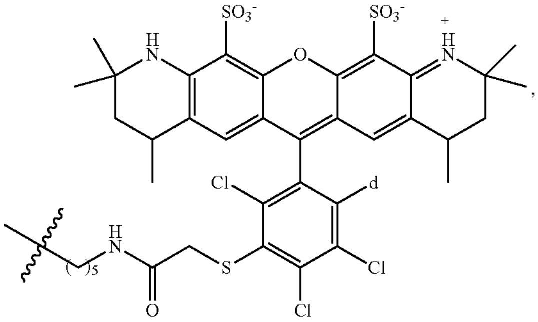
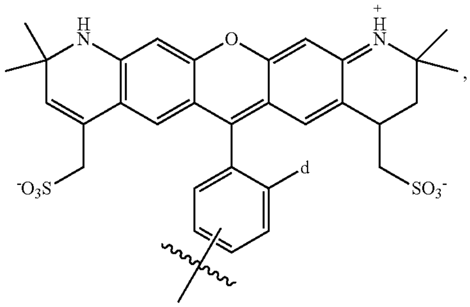
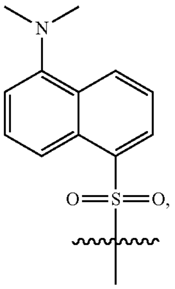
or a combination thereof, and wherein d is —C(O)O⁻, —COOH, or

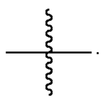

Prior to cleavage from a resin, the compounds described herein can contain one or more proximity induced modulator elements. When present, the degradation machinery recruiters are preferably in one or more of Z, Y1, Y1', Y4, or Y4'. Proximity induced modulator elements are described in Smith, et al., Bioorg. Med. Chem. Lett. 2008, 18(2): 5904-5908; Buckley, et al., ACS Chem. Biol. 2015, 10(8): 1831-1837; Jarvis, Chemical and Engineering News, Feb. 19, 2018, 96(8); Wang, et al., Acta Pharmaceutica Sinica B 2020, 10(2), 207-238; Takahashi, et al., Molecular Cell 2019, 76(5), 797-810; Banik, et al., ChemRxiv Nov. 11, 2019; Lai and Crews, Nat. Rev. Drug Discov. 2017, 16(2), 101-114; and Ding, et al., Trends in Pharmacological Sciences 2020, 41(7), 464-474; Siriwardena, et al., J. Am. Chem. Soc., 2020, 142 (33), 14052-14057; Costales, et al., Proc. Natl. Acad. Sci. USA, 2020, 117(5), 2406-2411; Yamazoe, et al., J. Med. Chem., 2020, 63, 2807-2813; Petrilli, et al., Cell Chem. Biol., 2020, 27(1), 32-40e; the contents of which are herein incorporated by reference in their entirety.

In some forms, the compound is defined by Formula I, as described above, except that Y1, Y1', Y4, and Y4' independently contain a proximity induced modulator element.

In some forms, the compound is defined by Formula I, as described above, except that Y2 is unsubstituted $C_1$-$C_3$ alkylene.

In some forms, the compound is defined by Formula I, as described above, except that Y4 is a substituted alkyl, preferably containing a substituted amide, or Y4 is a substituted amide.

In some forms, the compound is defined by Formula I, as described above, except that Y4 contains the proximity induced modulator element.

In some forms, the compound is defined by Formula I, as described above, except that the compound has a structure:

Formula XVI

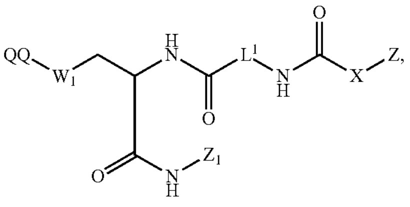

wherein Z1 is the proximity induced modulator element.

In some forms, the compound is defined by Formulae I and XVI, as described above, except that the proximity induced modulator element is a VHL ligand (such as VHL ligand 1), a pomalidomide, a thalidomide, a lenalidomide, a foretinib, a RIPK2, a dBET1, a SIRT2, a nutlin PROTAC (such as SARM-nutlin PROTAC, RG7112, idasanutlin, etc), cGMP modification/S-guanylation degradation tag (AUTAC), glycopeptide ligand for CI-M6PR (LYTAC), hydrophobic tagging (HyT, such as Halo-Tag fusion), beta-TrCP based PROTAC, MDM2 based PROTAC, bestatin esters (specific and non-genetic inhibitor-of-apoptosis proteins (IAPs)-dependent protein eraser), autophagosome-tethering compound (ATTEC), cell inhibitor of apoptosis protein (cIAP), KEAP1-dependent peptide PROTAC, PhosphoProtac, HaloProTac, endosome targeting chimeras (ENDTACs), phosphatase recruiting chimeras (PhoRC), Arg $(BOC)_3$ moiety, ribonuclease targeting chimeras (RIBOTACs), or a combination thereof.

Prior to cleavage from a resin, the compounds contain one or more small molecule moieties. The small molecule moieties have a molecular weight less than 2,500 Da. In some forms, the small molecule moieties have a molecular weight between 50 Da and 2,500 Da, inclusive. In some forms, the small molecule moieties have a molecular weight between 70 Da and 2,500 Da, inclusive.

A small molecule moiety can be located, preferably, at one or more of Z, Y1, Y1', Y4, or Y4'. Preferably, the small molecule moiety contains one or more chemical moieties such as primary alcohols, secondary alcohols, phenols, primary amines, secondary amines, tertiary amines, anilines, thiols, hydroxyamines, carboxyls, or a combination thereof, for covalent attachment to the rest of the compound. In some forms, the small molecule moiety, when present, is a therapeutic, diagnostic, or prophylactic agent.

In some forms, the compound is defined by Formulae I and X-XVI, as described above, except that W1 contains —OC(O)—, —C(O)O—, $—NR_2C(O)—$, $—NR_2—$, —C(O)—, —C(O)S—, —SC(O)—, or —NHNHC(O)—, preferably —OC(O)— or —C(O)O—.

In some forms, the compound is defined by Formulae I and X-XVI, as described above, except that QQ is selected from trityl resins (such as trityl chloride resins, 2-chlorotrityl chloride resins, 4-carboxytrityl resins, 4-methyltrityl chloride resins, 2-hydrazine trityl resins, and 4-methoxytrityl chloride resins), hydrazinobenzyol resins, Dawson Dbz AM resins, sulfonamide resins, HMBA resins, Merrifield resins, PAM resins, BHA resins, MBHA resins, Wang resins, brominated Wang resins, 4-nitrobenzophenone oxime resins, 4-(hydroxymethyl)phenoxyacetic acid resins, HMPB resins, Rink acid resins, Rink amide resins, PAL resins, Sieber amide resins, 4-sulfoamoylbenzoyl resins, aminoalkylated resins, hydroxyalkylated resins, brominated polystyrene resins, bromoalkylated resins, acrylamide-PEG copolymer resins, 4-(4-formyl-3-methoxyphenoxy)ethyl resins, melamine resins, acrylate resins, epoxy resins, urethane resins, silicone resins, fluoropolymer resins, well plates, and a combination thereof. Preferably, QQ is one or more trityl resins (such as trityl chloride resins, 2-chlorotrityl chloride resins, 4-carboxytrityl resins, 4-methyltrityl chloride resins, and 4-methoxytrityl chloride resins). In other preferred forms, QQ is one or more Sieber amide resins.

In some forms, the compound is defined by Formula I, as described above, except that QQ is present and a bond is present between QQ and W1, one or more of Z, Y1, Y1', Y4, and Y4' independently contain a proximity induced modulator element.

In some forms, the compound is defined by Formula I, as described above, except that QQ is present and a bond is present between QQ and W1, one or more of Y1, Y1', Y4, and Y4' independently contain an isocyanate, a carboxyl, an amine, an isonitrile, an N-hydroxyacyl, a hydroxyl, a thiol, a trialkylsilyl ether (such as trimethylsilyl ether), or a combination thereof.

In some forms, the compound is defined by Formula I, as described above, except that QQ is present and a bond is present between QQ and W1, one of Z, Y1, Y1', Y4, and Y4' contains the proximity induced modulator element, and the other of Y1, Y1', Y4, and Y4' contains an isocyanate, a carboxyl, an amine, an isonitrile, an N-hydroxyacyl, a hydroxyl, a thiol, a trialkylsilyl ether (such as trimethylsilyl ether), or a combination thereof.

In some forms, the compound is defined by Formula I, as described above, except that QQ is present and a bond is present between QQ and W1, and Z contains a proximity induced modulator element.

In some forms, the compound is defined by Formula I, as described above, except that QQ is present and a bond is present between QQ and W1, Z, Y1, Y1', Y4, and Y4' independently contain a proximity induced modulator element, and Y4 is a substituted amide.

In some forms, the compound is defined by Formula I, as described above, except that QQ is present and a bond is present between QQ and W1, Z, Y1, Y1', Y4, and Y4' independently contain a proximity induced modulator element, Y2 is unsubstituted $C_1$-$C_3$ alkylene (preferably $C_1$ alkylene) and Y1 and Y1' are hydrogen.

In some forms, the compound is defined by Formula I, as described above, except that QQ is present and a bond is present between QQ and W1, Z contains the proximity induced modulator element, and Y4 contains a carboxyl, amine, isonitrile, N-hydroxyacyl, hydroxyl, thiol, trialkylsilyl ether (such as trimethylsilyl ether), or a combination thereof.

In some forms, the compound is defined by Formula I, as described above, except that the compound has a structure:

Formula XVII

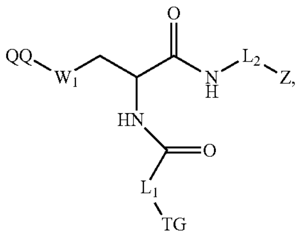

wherein TG is an isocyanate, a carboxyl, an amine, an isonitrile, an N-hydroxyacyl, a hydroxyl, a thiol, or a trialkylsilyl ether (such as trimethylsilyl ether), and wherein Z is the proximity induced modulator element, and L2 is optionally absent.

In some forms, the compound is defined by Formulae I and XVII, as described above, except that W1 contains —OC(O)—, —C(O)O—, —$NR_2$C(O)—, —NR—, —C(O)—, —C(O)S—, —SC(O)—, —NHNHC(O)—, or a combination thereof, preferably —OC(O)— or —C(O)O—.

In some forms, the compound is defined by Formulae I and XVII, as described above, except that QQ is selected from trityl resins (such as trityl chloride resins, 2-chlorotrityl chloride resins, 4-carboxytrityl resins, 4-methyltrityl chloride resins, 2-hydrazine trityl resins, and 4-methoxytrityl chloride resins), hydrazinobenzyol resins, Dawson Dbz AM resins, sulfonamide resins, HMBA resins, Merrifield resins, PAM resins, BHA resins, MBHA resins, Wang resins, brominated Wang resins, 4-nitrobenzophenone oxime resins, 4-(hydroxymethyl)phenoxyacetic acid resins, HMPB resins, Rink acid resins, Rink amide resins, PAL resins, Sieber amide resins, 4-sulfoamoylbenzoyl resins, aminoalkylated resins, hydroxyalkylated resins, brominated polystyrene resins, bromoalkylated resins, acrylamide-PEG copolymer resins, 4-(4-formyl-3-methoxyphenoxy)ethyl resins, melamine resins, acrylate resins, epoxy resins, urethane resins, silicone resins, fluoropolymer resins, well plates, and a combination thereof. Preferably, QQ is one or more trityl resins (such as trityl chloride resins, 2-chlorotrityl chloride resins, 4-carboxytrityl resins, 4-methyltrityl chloride resins, and 4-methoxytrityl chloride resins). In other preferred forms, QQ is one or more Sieber amide resins.

B. Compound Libraries

In some forms, the compounds represented by any of Formulae I, III-XVII, VII', and XIV' are in a composition containing a plurality of the compounds, forming a library of compounds.

Every compound within the above definition is considered to be specifically disclosed herein. Further, every subgroup that can be identified within the above definition is considered to be specifically disclosed herein. Further, every chemical group that can be identified within the above definition is considered to be specifically disclosed herein. As a result, it is specifically contemplated that any compound, subgroup of compounds, or chemical moiety can be either specifically included for or excluded from use or included in or excluded from a list of compounds. For example, any one or more of the compounds described herein, with a structure depicted herein, or referred to in the Schemes, Figures, Tables, or the Examples herein can be specifically included, excluded, or combined in any combination, in a set or subgroup of such compounds or from chemical moieties of these compounds. Such specific sets, subgroups, chemical moieties inclusions, and exclusions can be applied to any aspect of the compositions and methods described here. For example, a set of compounds that specifically excludes one or more particular compounds can be used or applied in the context of compounds per se (for example, a list or set of compounds), compositions including the compound, any one or more of the disclosed methods, or combinations of these. Different sets and subgroups of compounds or chemical moieties with such specific inclusions and exclusions can be used or applied in the context of compounds per se, compositions including one or more of the compounds, or any of the disclosed methods. All of these different sets and subgroups of compounds or chemical moieties, and the different sets of compounds, compositions, and methods using or applying the compounds, are specifically and individually contemplated and should be considered as specifically and individually described. For example, the following can be specifically included or excluded, as a group or individually, from any compounds per se (for example, a list or set of compounds), compositions including the compound, or any one or more of the disclosed methods, or combinations of these. For example, the compounds of Formula I can exclude (i) Z being an amino acid residue, (ii) Z being a lysine residue, (iii) Z being an amino acid residue when W is —NHC(O)NH—, (iv) Z being a lysine residue when W is —NHC(O)NH—, or (v) glutamate-urea-lysine. In a further example, the compound of Formula I (e.g., a compound of Formulae III-VIII) is not a compound disclosed in any of WO2018/067615; WO2012/167223; WO2016/019391; WO2017/075630; WO2017/075631; US2013/0261023; and U.S. Pat. No. 7,932,213.

III. Methods of Making and Reagents Therefor

Described herein are methods for modifying small molecules. The methods can be generalized for the efficient and/or unbiased addition of chemical moieties to small molecules to generate libraries of compounds for use in high-throughput screening settings. Unbiased addition indicates a preference for modifying the small molecules once, when the small molecules have multiple potential locations that can be modified. Preferably, the method involves solid phase synthesis and isocyanate-based chemistry. When an isocyanate chemistry is involved, the isocyanate can react with a number of nucleophilic functional groups, such as —OH, —NH— or —$NH_2$, and —SH to form a carbamate, urea, and carbamothioate bonds, respectively.

Small molecules usually have multiple sites that react with functional groups, such as an isocyanate. If these functional groups (such as isocyanate) are freely floating in solution, they can react with all available sites on the small molecules, potentially resulting in a loss of activity of the small molecules. To avoid this problem, the chemical moieties (containing functional groups, such as isocyanate) to be added to a library of small molecules are first conjugated to a resin for subsequent reaction with the small molecule.

A non-limiting prophetic schematic showing the addition of a chemical moiety to a small molecule is shown in FIG. 1. The resin can be any suitable resin described herein, but a Sieber amide resin was used. The resin can be deprotected, by removing the Fmoc group in the presence of piperidine, exposing an amino group (e.g., a primary amino group). An organic compound 1 (such as an Fmoc protected amino acid) can be reacted with the resin under basic conditions. The reaction can create an amide bond between the compound 1 and the resin, forming a new compound 2. The bond between compound 1 and the resin is not limited to an amide bond. In the case of a Sieber amide resin, the bond between an amide and a xanthen-3-yloxy group on the resin is cleaved. Generally, the bond that is cleaved to remove the resin can be a bond that is easily cleaved under conditions (e.g., mild acid conditions) that do not degrade the end product. The compound can be deprotected, by removing the Fmoc group in the presence of piperidine, exposing an amino group (e.g., a primary amino group). In some forms, the exposed amino group can be directly converted to an isocyanate in the presence of triphosgene, diisopropylethylamine and dichloromethane (DCM). In some forms, a linker represented in FIG. 1 as 2*a* (succinic anhydride) or 2*b* (organic compound containing two reactive groups, e.g., carboxylic acid) can be reacted with the exposed amine to display a carboxyl group (as shown in 3*a* and 3*b*) capable of further reaction with another organic compound. Resin-immobilized compound 3*a* or 3*b* can be converted to compound 4*a* or 4*b* containing an isocyanate group in the presence of a suitable reagent such as either $SOCl_2/NaN_3$ followed by heating under argon, or diphenylphosphoryl azide (DPPA), dimethyl formamide (DMF), and triethylamine under heat, resulting in the isocyanate via a Curtius rearrangement reaction. Isocyanate-functionalized resin (4*a* or 4*b*) can then be mixed with small molecules of interest. The mixing with the small molecules of interest can be in a plate-based format (5*a* or 5*b*). Preferably, after unreacted material has been removed (such as via wash steps), the modified small molecules (6*a* or 6*b*) can be cleaved from the resin under mild conditions (such as under 5% trifluoroacetic acid (TFA)). These molecules (resin bound or free) can then be used to treat cells, cell lysates, proteins, or pure protein to study small molecule-protein interactions of interest.

Preferably, the solid-phase reaction allows only one resin-immobilized functional group (such as isocyanate) to react per small molecule. In a microarray setting, this strategy allows the isocyanate to bind to a small molecule in different orientations facilitating the examination of the full range of activity of a given molecule. Additional benefits of coupling the small molecule to resin include the ability to obtain a desired concentration of bifunctionalized small molecules with minimal starting material and ease of purification.

As discussed above, any suitable resin can be used. In this non-limiting example, a Sieber amide resin containing a polystyrene bead was chosen, because polystyrene can withstand the solvents used in the Curtius rearrangement reaction and can swell under those conditions. Resin swelling can space out the chemical groups and help prevent the functional groups (such as isocyanate groups) from reacting with each other. In some forms the resins are loaded, such that between 1% and 80%, inclusive, 1% and 75%, inclusive, 1% and 70%, inclusive, 1% and 65%, inclusive, 1% and 60%, inclusive, 1% and 55%, inclusive, 1% and 50%, inclusive, 5% and 80%, inclusive, 10% and 80%, inclusive, 15% and 80%, inclusive, 20% and 80%, inclusive, 30% and 60%, inclusive, 50% and 60%, inclusive, 5%, 10%, 15%, 20%, 25%, 30%, 35%, 40%, 45%, 50%, 55%, 60%, 65%, 70%, or 75% of functional groups on their surfaces are modified. Further, the Sieber amide resin can be chosen, because it (1) can allow the small molecules to be cleaved off the resin in mildly acidic conditions that will not alter the chemical structure of the small molecule and (2) does not alter the properties of the molecule (6*a* or 6*b*) after cleavage. This method is compatible with a plate-based format and automated liquid handlers.

Figure 2:
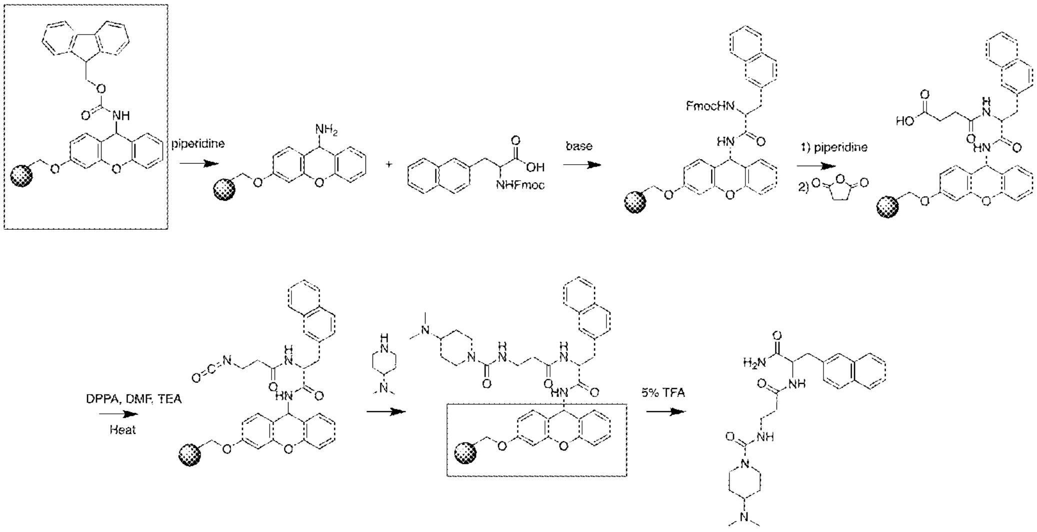
FIG. 2 is a schematic reaction showing how a small molecule or small molecules in chemical libraries can be modified contain naphthalene. The structures or moieties in the rectangle denote a resin prior to and after attachment of a chemical compound. The resin is a Sieber amide resin with the circle containing polystyrene. The resin can also be any of the other resins listed below.

FIG. 2 shows a schematic for rapidly introducing another small molecule moiety. In this non-limiting example, an organic compound was generated containing a naphthyl. The resin can be deprotected, by removing the Fmoc group in the presence of piperidine, exposing an amino group (e.g., a primary amino group). An organic compound (such as an Fmoc protected 2-napthyl)-L-alanine) is reacted with the resin (such as Sieber amide resin) under basic conditions. The reaction creates an amide bond between the organic compound and the resin. The bond between the compound and the resin is not limited to an amide bond. In the case of a Sieber amide resin, the bond between an amide and a xanthen-3-yloxy group on the resin is cleaved. Generally, the bond that is cleaved to remove the resin can be a bond that is easily cleaved under conditions (e.g., mild acid conditions) that do not degrade the end product. The compound is deprotected, by removing the Fmoc group in the presence of piperidine, exposing an amino group (e.g., a primary amino group). In some forms, the exposed amino group can be directly converted to an isocyanate in the presence of triphosgene, diisopropylethylamine and DCM. In some forms, a linker represented in FIG. 2 as succinic anhydride can be reacted with the exposed amine to display a carboxyl group capable of further reaction with another organic compound. The resin-immobilized organic compound can be converted to another compound containing an isocyanate group in the presence of a suitable reagent such as either $SOCl_2/NaN_3$ followed by heating under argon, or diphenylphosphoryl azide (DPPA), DMF, and triethylamine under heat, resulting in the isocyanate via a Curtius rearrangement reaction. Isocyanate-functionalized resin can then be mixed with a compound that contains a desired functional group to be introduced. In this non-limiting case, the isocyanate was reacted with 4-(dimethylamino)piperidine forming a urea bond. The compound containing the naphthyl can be cleaved from the resin under mild conditions (such as under 5% TFA). Where the naphthyl is replaced by a compound or moiety that fluoresces, these molecules (resin bound or free) can then be used to treat cells, cell lysates, proteins, or pure protein to study small molecule-protein interactions of interest. This method can be used for biological and medical labels.

Figure 3:
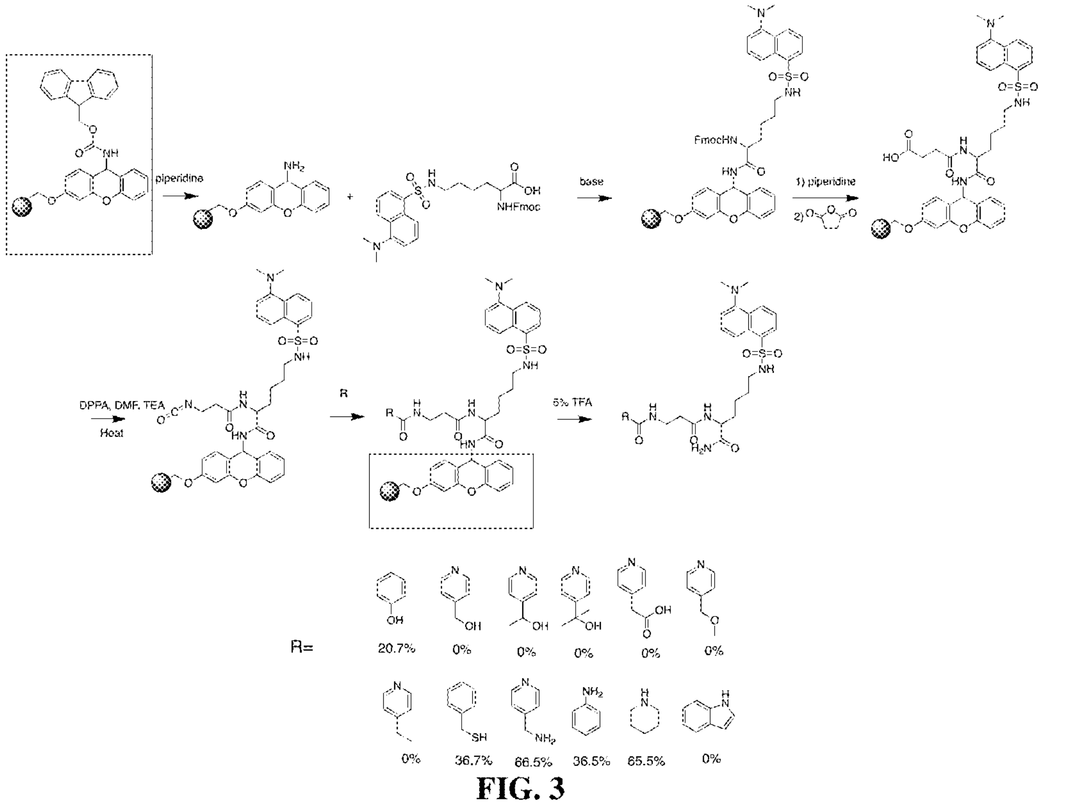
FIG. 3 is a schematic that compares the reactivity of different nucleophilic groups with an isocyanate-functionalized fluorophore. The fluorophore is 1,5-danysl-L-lysine. The structures or moieties in the rectangle denote a resin prior to and after attachment of a chemical compound. The resin is a Sieber amide resin with the circle containing polystyrene. The resin can also be any of the other resins listed below. R represents a small molecule.

FIG. 3 is a schematic that compares the reactivity of different nucleophilic groups with an isocyanate-functionalized fluorophore. The fluorophore is 1,5-danysl-L-lysine. The resin can be deprotected, by removing the Fmoc group in the presence of piperidine, exposing an amino group (e.g., a primary amino group). An organic compound (such as an Fmoc protected 1,5-danysl-L-lysine) is reacted with the resin (such as Sieber amide resin) under basic conditions. The reaction can create an amide bond between the organic compound and the resin. The bond between the compound and the resin is not limited to an amide bond, and can be a bond that is easily cleaved under conditions (e.g., mild acid conditions) that do not degrade the end product. The compound can be deprotected, by removing the Fmoc group in the presence of piperidine, exposing an amino group (e.g., a primary amino group). In some forms, the exposed amino group can be directly converted to an isocyanate in the presence of triphosgene, diisopropylethylamine and DCM. In some forms, a linker represented in FIG. 3 as succinic anhydride can be reacted with the exposed amine to display a carboxyl group capable of further reaction with another organic compound. In some forms, the resin-immobilized organic compound can be converted to another compound containing an isocyanate group in the presence of a suitable reagent such as either $SOCl_2/NaN_3$ followed by heating under argon, or diphenylphosphoryl azide (DPPA), DMF, and triethylamine under heat, resulting in the isocyanate via a Curtius rearrangement reaction for subsequent reaction with a small molecule. In this non-limiting case, a fluorophore (dansyl) was introduced by reacting the isocyanate with either 4-ethylpyridine, 4-(aminomethyl) pyridine, benzyl mercaptan, 4-(methoxymethyl)pyridine, piperidine, aniline, R-(+)-alpha-methyl-4-pyridinemethanol, 4-pyridylacetic acid hydrochloride, 4-pyridinemethanol, 2-(4-pyridiyl)-2-propanol, phenol, or indole. In the experiments, 4-ethylpyridine, 4-pyridylacetic acid hydrochloride, and 4-(methoxymethyl)pyridine were chosen as controls due to their poor nucleophilicity. Under the conditions, methods, and reagents described herein, 4-pyridinemethanol, R-(+)-alpha-methyl-4-pyridinemethanol, 2-(4-pyridiyl)-2-propanol, and indole did not work. It is believed that the nucleophilicities of R-(+)-alpha-methyl-4-pyiridinemethanol, 4-pyridinemethanol, 2-(4-pyridyl)-2-propanol, and indole by either (i) activating the alcohols with 2 mole percent DMAP in toluene at 80° C. for 1 hour before adding the solution to the isocyanate functionalized group of interest (dansyl), (ii) mixing the isocyanate functionalized group of interest (dansyl) with dibutyltin(II)-dilaurate (0.02 equivalents (eq.)) and the alcohol (2 equivalents) in toluene at 60° C. for 48 hours, (iii) mixing the isocyanate functionalized group of interest (dansyl, 1.1 eq.) with the alcohol (1 eq.), CuCl (0.1 eq), and pyridine (10 eq.) in toluene at 50° C. for 2 hours, or iv) stirring the indole (1 eq.) with NaH (60% dispersion in mineral oil, 2 eq.) in DMF at 0° C. for 1 hour and then adding the mixture to the isocyanate functionalized group, as in published studies (Valois-Escamilla, I; Alvarez-Hernandez, A; Rangel-Ramos, LF; Suarez-Castillo, OR; Ayala-Mata, F; Zepeda-Vallejo, G; *Tetrahedron Lett.* 2011, 52(29), 3726-3728; Sandmann, B.; Happ, B; Hager, MD; Vitz, J; Rettler, E; Burtscher, P; Moszner, N; Schubert, US. *Journal of Polymer Science, Part A: Polymer Chemistry* 2014, 52, 239-247; Amada, H, Sekiguchi, Y, Ono, N, Koami, T, Takayama, T, Yabuuchi, T, Katakai, H, Ikeda, A, Aoki, M, Naruse, T, Wada, R, Nozoe, A, Sato, M. *Bioorg. Med. Chem.* 2012, 20(24), 7128-7138; Bhat, A. H, Alavi, S, Grove, H. K, *Org. Lett.* 2020, 22, 224-229. Reactions with 4-(aminomethyl) pyridine, benzyl mercaptan, piperidine, aniline, and phenol had yields of 67%, 37%, 66%, 37%, and 21%, respectively. The compound containing the functional group of interest (dansyl) can be cleaved from the resin under mild conditions (such as under 5% TFA). These molecules (resin bound or free) can then be used to treat cells, cell lysates, proteins, or pure protein to study small molecule-protein interactions of interest.

Figure 4:
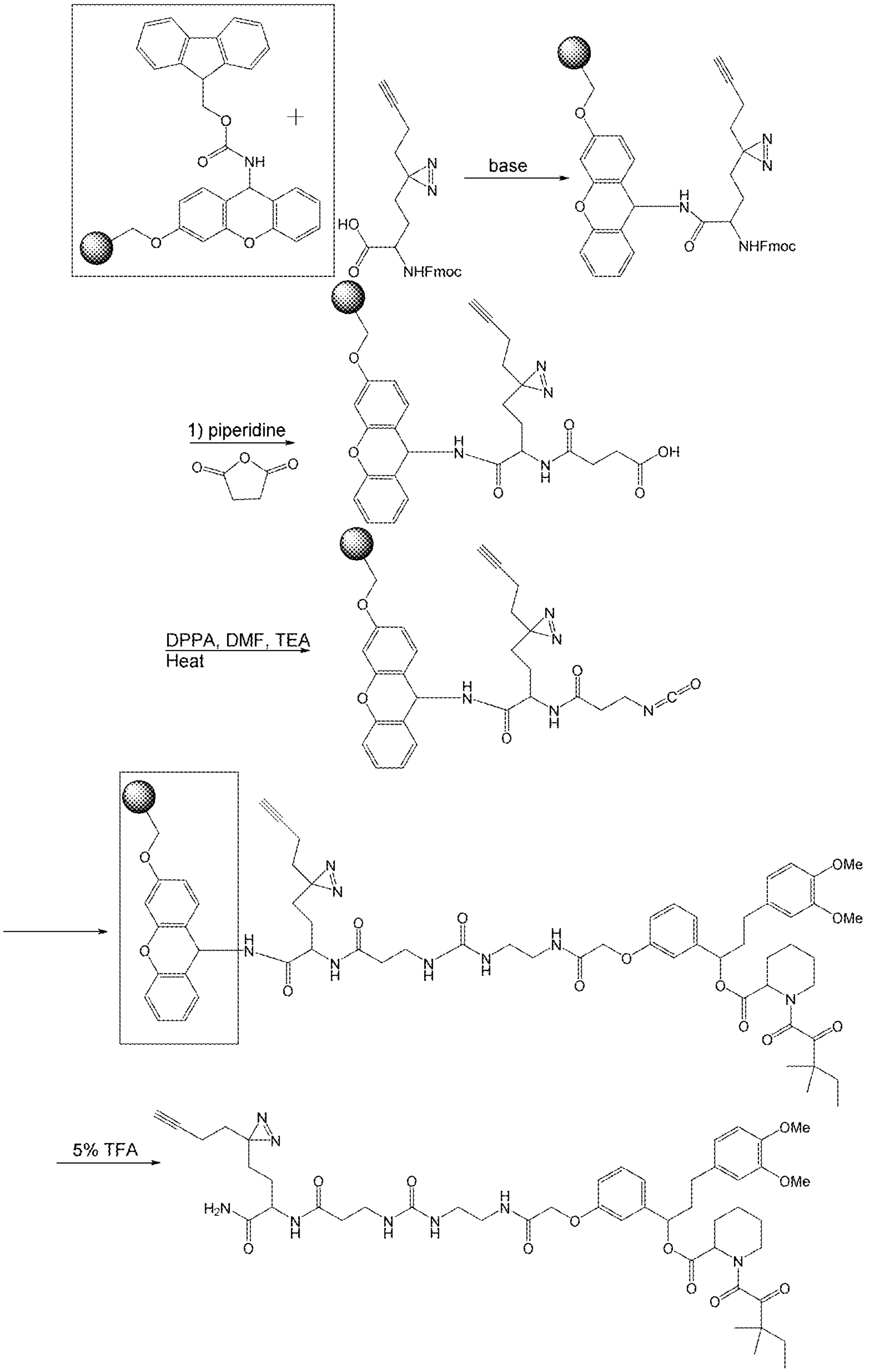
FIG. 4 is a schematic reaction showing how a small molecule or small molecules in chemical libraries can be functionalized to contain a photoactivatable group (e.g., a diazirine) and a "click" handle (such as an alkyne) using photo-aminononynoic acid (pANA). The small molecule is AP1497, i.e., an FKBP12 binder. The structures or moieties in the rectangle denote a resin prior to and after attachment of a chemical compound. The resin is a Sieber amide resin with the circle containing polystyrene. The resin can any of the other resins listed below.

FIG. 4 is a schematic for rapidly introducing two functions of interest to small molecules or small molecule libraries described herein. In this non-limiting example, an organic compound was generated containing a photoactivatable group (e.g., a diazirine) and a "click" handle (such as an alkyne) using photo-aminononynoic acid. Ultimately, such small molecules or small molecule libraries can be used to identify targets (such as proteins) that bind to the small molecules. The small molecule is an AP1497, i.e., an FKBP12 binder. In this non-limiting schematic, AP1497 can be modified to contain a diazirine and an alkyne. An organic compound (such as an Fmoc protected photo-aminononynoic acid) can be reacted with the resin (such as Sieber amide resin) under basic conditions. The reaction can create an amide bond between the organic compound and the resin. The bond between the compound and the resin is not limited to an amide bond. In the case of a Sieber amide resin, the bond between an amide and a xanthen-3-yloxy group on the resin is cleaved. Generally, the bond that is cleaved to remove the resin can be a bond that is easily cleaved under conditions (e.g., mild acid conditions) that do not degrade the end product. The compound can be deprotected, by removing the Fmoc group in the presence of piperidine, exposing an amino group (e.g., a primary amino group). In some forms, the exposed amino group can be directly converted to an isocyanate in the presence of triphosgene, diisopropylethylamine and DCM. In some forms, a linker represented in FIG. 4 as succinic anhydride can be reacted with the exposed amine to display a carboxyl group capable of further reaction with another organic compound. In some forms, the resin-immobilized organic compound can be converted to another compound containing an isocyanate group in the presence of a suitable reagent such as either $SOCl_2/NaN_3$ followed by heating under argon, or diphenylphosphoryl azide (DPPA), DMF, and triethylamine under heat, resulting in the isocyanate via a Curtius rearrangement reaction for subsequent reaction with a small molecule. In the case where the small molecule contains an electrophilic group, such as AP1497, a second organic compound (ethylene diamine) can be reacted with the small molecule, such as AP1497, first and optionally purified via high-performance liquid chromatography. A second reactive group on the second organic compound (e.g., an amine group) can next be reacted with isocyanate to form a urea bond. The compound (such as AP1497) containing the two functional groups of interest (such as a photoactivatable group and an alkyne) can be cleaved from the resin under mild conditions (such as under 5% TFA). These molecules (resin bound or free) can then be used to treat cells, cell lysates, proteins, or pure protein to study small molecule-protein interactions of interest. A product produced in this experiment was able to label recombinant human FKBP12-His and FKBP12-SNAP that had been exposed to UV irradiation with Alexa Fluor 647.

Figure 5:
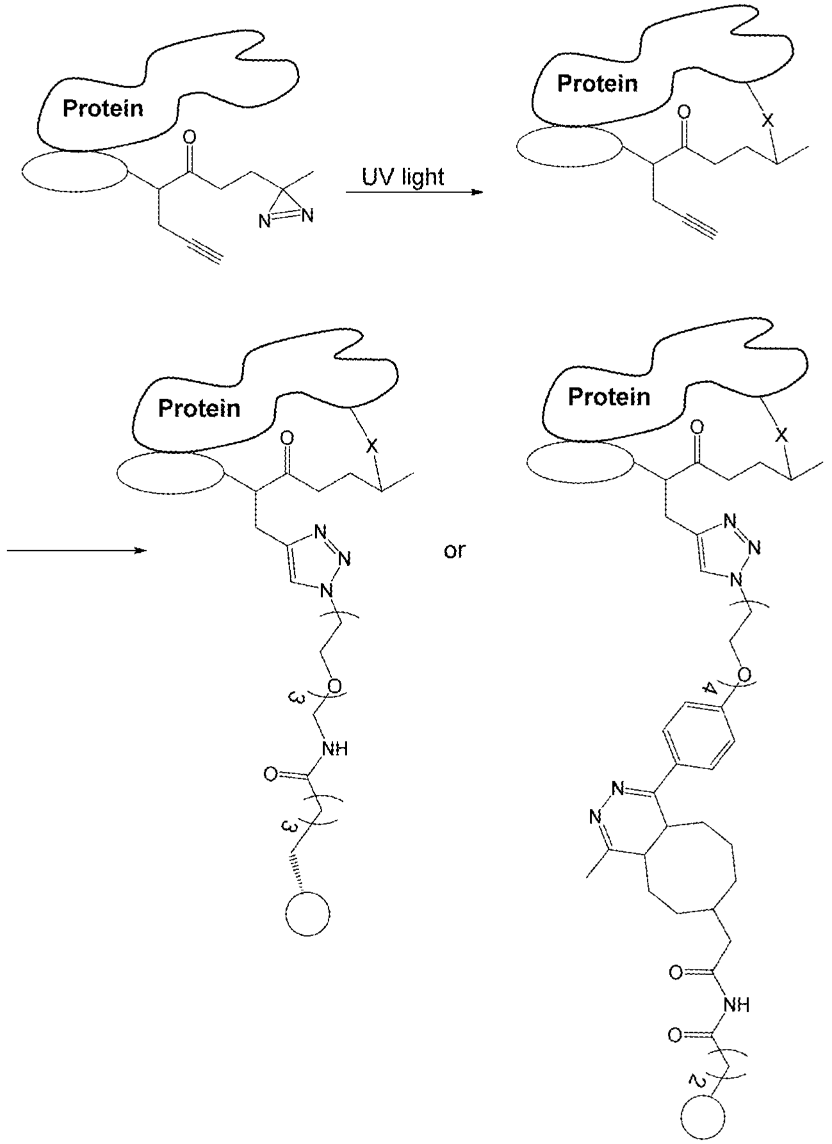
FIG. 5 is a schematic showing a small molecule-protein interaction. The photoactivatable group (diazirine) covalently attaches to any protein the small molecule is bound to after being exposed to ultraviolet light. The "click" handle (such as an alkyne) can then be used for enrichment or detection of the small molecule-protein interaction. The oval is a small molecule. The circle is biotin, a bead, or other substrate, such as a well plate.

FIG. 5 is a prophetic schematic showing how a non-limiting small molecule-protein interaction can be enriched for detection using a small molecule bifunctionalized to contain a photoactivatable group (such as a diazirine) and another functional group (such as a "click" handle, such as an alkyne) capable of reacting with another chemical group immobilized on a solid support. After exposing a compound, as described herein, to a protein, the complex (compound-protein) can be exposed to an appropriate radiation energy source (such as UV light). In the instant, non-limiting prophetic schematic, the photoactivatable group can form a highly reactive carbene that forms a covalent bond with a nearby portion of the protein. Next, the complex can be exposed to a surface containing a functional group (in this non-limiting example, an azide) capable of reacting with the "click" handle (such as alkyne) in the complex. Mobilization of the complex containing a covalent bond on the solid support ensures that the protein-small molecule interaction is enriched for further analysis and characterization.

In non-limiting examples, proteins in complexes containing an alkyne group were immobilized on an azide-functionalized well plate, and the proteins were detected with an ELISA. Details of the experiments are provided in the examples.

Figure 6:
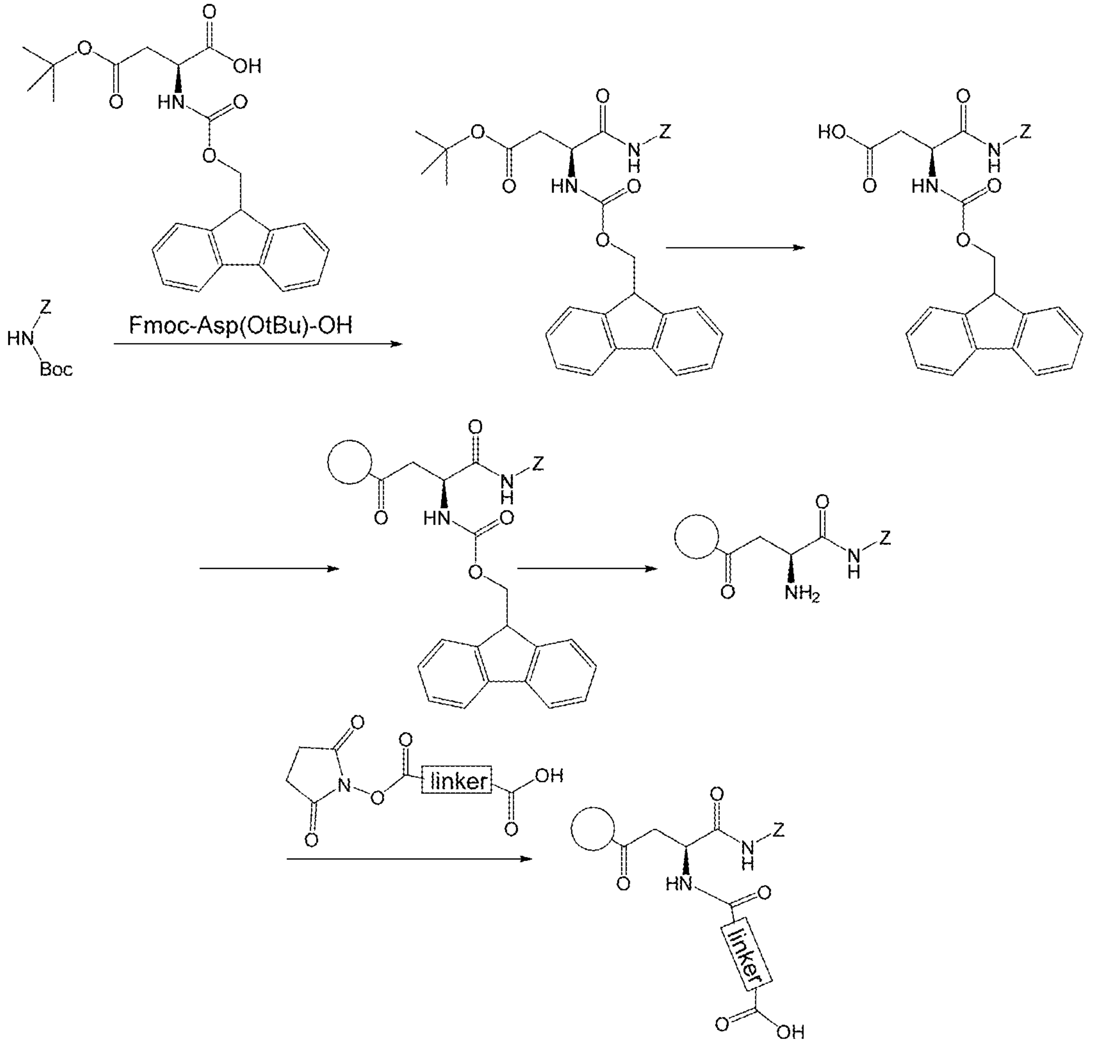
FIG. 6 is a schematic reaction showing how resins can be modified to include a proximity induced modulator element and a functional group that can be further converted to an isocyanate. As shown, the functional group is a carboxyl group attached to a "linker." The circle denotes a resin.
Figure 6:
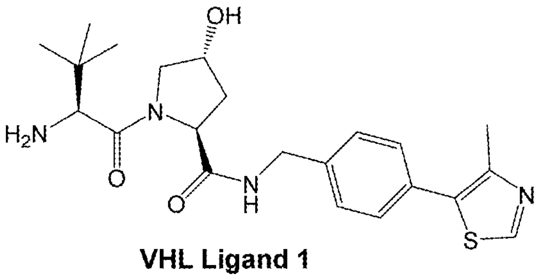
Figure 6:
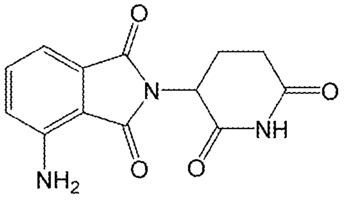
Figure 6:
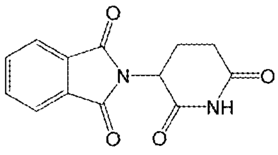
Figure 6:
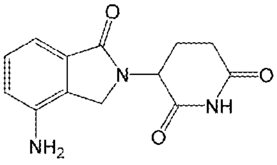

FIG. 6 is a prophetic schematic reaction showing how resins can be modified to include a proximity induced modulator element and a functional group that can be further converted to an isocyanate. In a non-limiting example, a proximity induced modulator element, denoted Z, containing a Boc-protected amino group, can be deprotected using means known to those of skill in the art, such as under anhydrous acid conditions (TFA in DCM, HCl in $CH_3OH$), followed by reaction with an organic compound, such as Fmoc-Asp(OtBu)—OH. The t-butyl ester can be selectively hydrolyzed using TFA to expose the protected carboxylic group. The exposed carboxyl group can react with a group on a resin, such as a trityl chloride resin under basic conditions via a mechanism discussed above. The Fmoc protecting group can be subsequently cleaved using piperidine, as discussed above to expose an amino group. In some forms, the exposed amino group can be directly converted to an isocyanate in the presence of triphosgene, diisopropylethylamine and DCM. In some forms, a linker (organic compound containing two reactive groups, e.g., carboxylic acid) can be reacted with the exposed amine to display a carboxyl group capable of further reaction with another organic compound. In some forms, the resin-immobilized compound can be converted to a compound containing an isocyanate group in the presence of a suitable reagent such as either $SOCl_2/NaN_3$ followed by heating under argon, or diphenylphosphoryl azide (DPPA), DMF, and triethylamine under heat, resulting in the isocyanate via a Curtius rearrangement reaction.

These compounds (resin bound or free) can then be provided for a suitable use. A suitable use can be for further modification to include a small molecule therapeutic, diagnostic, or prophylactic agent. Another suitable use can be for treating cells, cell lysates, proteins, or pure protein to study small molecule-protein interactions of interest.

Figure 7A:
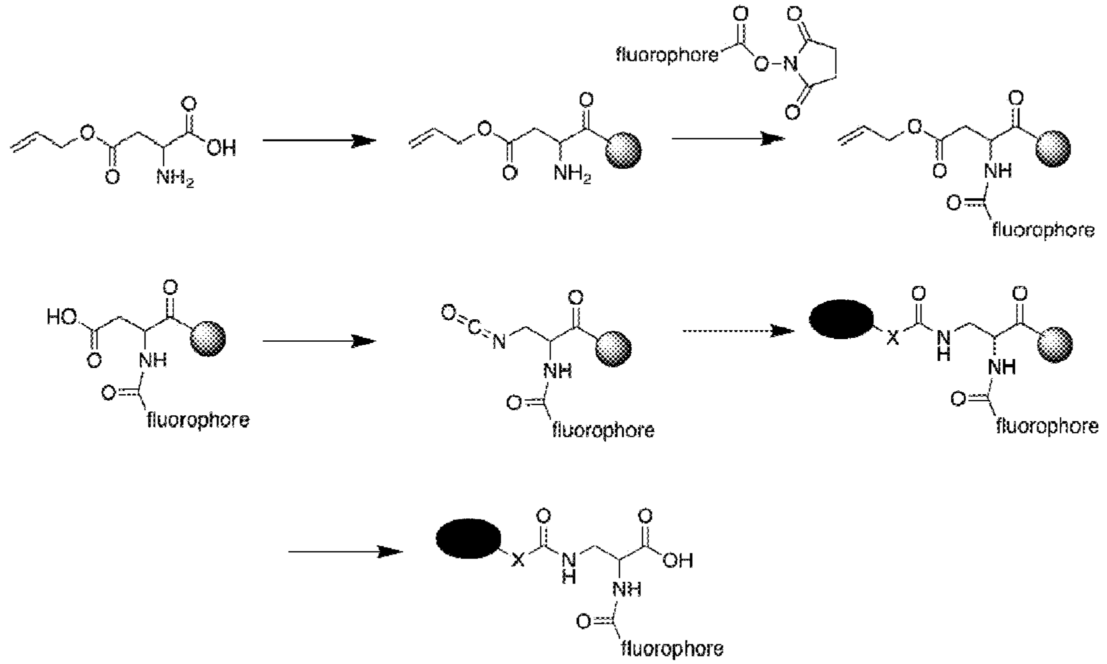
FIGS. 7A and 7B are schematic reactions showing how a small molecule or small molecules in chemical libraries can be functionalized to contain a fluorophore. The circle and oval denote a resin and a small molecule, respectively.
Figure 7B:
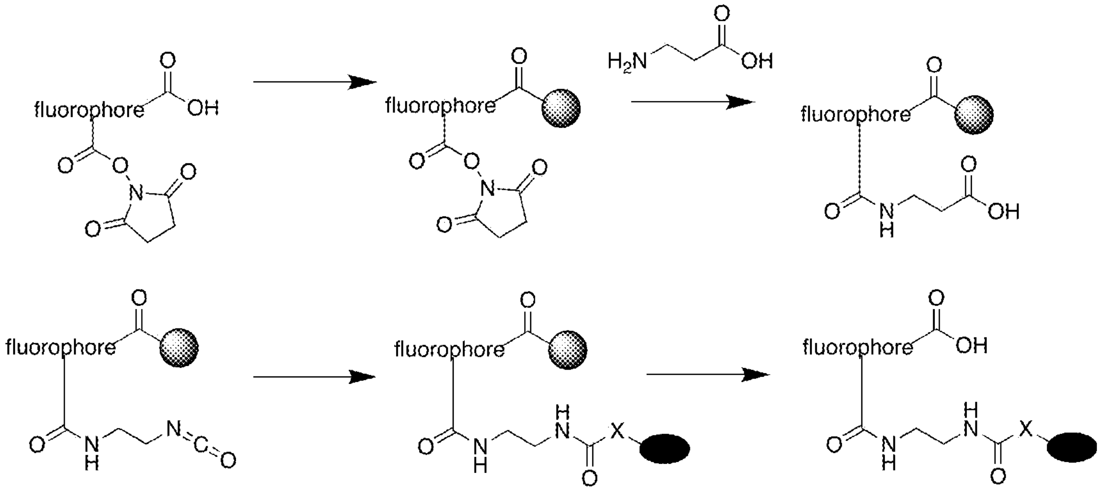

FIGS. 7A and 7B are prophetic schematic reactions showing how a small molecule or small molecules in chemical libraries can be functionalized to contain a fluorophore. These reactions generally proceed using reagents and/or under reaction conditions discussed above. In FIG. 7A, the fluorophore can be attached to the rest of the compound at one position. In FIG. 7B, the fluorophore can be attached to the rest of the compound at two or more positions, preferably at two positions. These molecules (resin bound or free) can then be used to treat cells, cell lysates, proteins, or pure protein to study small molecule-protein interactions of interest.

Analytical techniques (such as liquid chromatography-mass spectrometry) known to those of skill in the art can be used to confirm the generation of the products at each synthesis step.

Although the figures have been shown using reagents (such as either $SOCl_2/NaN_3$ and heating or diphenylphosphoryl azide (DPPA), DMF, and triethylamine under heat) that proceed via the Curtius rearrangement to form an isocyanate from a carboxyl group, other types of reactions and reagents can be used to generate isocyanate groups from various functional groups. For example, (i) the reaction of an amine with triphosgene in diispropylethylamine in dry dichloromethane at 0° C. converts the amine to an isocyanate (Mosayebnia, et al., Iranian Journal of Pharmaceutical Research 2018, 71(3), 917-926), (ii) alkyl isocyanates are prepared by treatment of alcohols, thiols and trimethylsilyl ethers with triphenylphosphine/2,3-dichloro-5,6-dicyanobenzoquinone/Bu4NOCN in acetonitrile (Akhlaghinia, Synthesis, 2005, 1955-1958); (iii) isonitriles are oxidized to isocyanates by DMSO as the oxidant catalyzed by trifluoroacetic anhydride (Ganem, Org. Lett., 2011, 13, 2584-2585); (iv) N-hydroxyacyls are converted to isocyanates in the presence of nosyl chloride in diispropylethylamine and tetrahydrofuran (Miller, Org. Lett., 2013, 15, 602-605).

IV. Methods of Using

The methods can be used for the rapid and efficient modification of small molecules or libraries of small molecules. In cases where the small molecules contains two or more nucleophiles and/or electrophiles, preferably two or more nucleophiles, the methods modify the small molecules in an unbiased way, because, unlike traditional methods designed to modify specific groups on small molecules, the method is not restricted to any particular group on the small molecule. Unbiased way indicates a preference for modifying the small molecules once, when the small molecules have multiple potential locations that can be modified. Accordingly, several orientations of the small molecules are present in the library, thereby facilitating a broader assessment of the activities of the small molecules. This is because a small molecule's activity can depend on the physicochemical properties of a surface that the small molecule presents to a target (such as a protein), especially in assays that immobilize the small molecules in microarray plates and other solid support systems. Accordingly, for each small molecule, several molecules to generate libraries of compounds for use in high-throughput screening settings.

The compounds can be used in target identification, drug discovery, chemical library production, high-throughput screening, fluorophore conjugation, chemiluminescent compound conjugation, creation of proximity induced modulators (e.g., protein degraders), or a combination thereof. The compounds can be used to detect the binding of a receptor to a small molecule incorporated into the compound. The compounds can also be used for optical imaging, such as when they contain a fluorophore or chemiluminescent compound. Further, in a drug discovery pipeline that involves high-throughput screening, the compounds can be used for target identification, studying mechanism of action and/or binding of the target, and for subsequent structure-activity relationships using the identified targets.

EXAMPLES

Example 1: Functionalization of Succinic Anhydride Modified 3-(2-napthyl)-L-alanine with 4-(dimethylamino)piperidine

Materials and Methods

Sieber amide resin (Novabiochem, Cat 8550080025, 0.62 mmol/g, 1 eq., 0.673 mmol) was swelled in anhydrous dimethylformamide (DMF) (10 mL) in a reaction syringe (Supelco, Cat #57118-U) for 30 minutes. DMF was removed under reduced pressure. The resin was deprotected by stirring with 20% v/v piperidine/DMF for 20 minutes. This was repeated. The resin was then washed three times with DMF. While the resin was being deprotected, N-Fmoc-3-(2-napthyl)-L-alanine (Combi Blocks Inc, Cat #SS-0101, 0.2 eq.) and hexafluorophosphate azabenzotriazole tetramethyl uronium (HATU) (0.2 eq.) were stirred in anhydrous DMF (2 mL) at room temperature for 30 minutes in a separate flask. The resin was reswelled in anhydrous DMF (10 mL). The N-Fmoc-3-(2-napthyl)-L-alanine and HATU solution was added to the resin. N,N-Diisopropylehylamine (DIPEA) (0.4 eq.) was then added to the solution and was allowed to stir for 3 hours at room temperature. The resin was then washed three times with DMF. Unreacted sites on the resin were quenched by adding a solution of 5% acetic anhydride and 10% triethylamine in DMF (7 mL) for 30 min. The resin was then washed three times with DMF, three times with methanol, and then dried under reduced pressure. A test cleavage was performed, where a few beads of resin were collected, resuspended in 5% TFA in DCM, placed on a shaker for 30 min, then filtered through cotton and analyzed via LCMS. To assess resin loading, ten milligrams of dry resin were weighed out and set aside for quantification. The resin was then reswelled in anhydrous DMF (10 mL) for 30 minutes. N-Fmoc-3-(2-napthyl)-L-alanine was deprotected by adding 20% v/v piperidine/DMF for 20 minutes. This was repeated. A solution of succinic anhydride (0.6 eq.) and DIPEA (0.4 eq.) in DMF (10 mL) was added to the resin for 1.5 hours. The resin was then washed three times with DMF, three times with methanol, and then dried under reduced pressure. A test cleavage was performed. The resin was then reswelled with anhydrous toluene (4 ml) under argon atmosphere for 30 minutes. Triethylamine (1 eq.) and DPPA (Sigma-Aldrich Inc, Cat #178756, 1 eq.) were added to the resin at room temperature and stirred for two hours. 4-(dimethylamino)piperidine (Combi Blocks Inc., Cat #OR-2661, 0.24 eq.) was added to the solution and stirred for 20 hours at 75° C. The resin was then quenched with anhydrous methanol (10 mL) for 10 minutes, then washed 3 times with methanol. The resin was cleaved with 5% TFA in DCM for 18 hours, filtered through cotton, and analyzed by NMR. The loading of the beads was quantified using standard protocols (aapptec technical support information bulletin 1198, downloaded Apr. 1, 2021). Maleic acid was added to the NMR samples as an internal standard to quantify reaction efficiency based on resin loading.

Results

The functionalization of succinic anhydride modified 3-(2-napthyl)-L-alanine with 4-(dimethylamino)piperidine was confirmed by NMR. The yield of the reaction is calculated to be 57% based on the maleic acid internal standard. $^{1}H$ NMR (500 MHz, $(CD_3)_2SO$) δ (ppm)=8.16 (t, J=8.1 Hz, 1H), 7.93-7.77 (m, 4H), 7.73 (s, 1H), 7.52-7.37 (m, 4H), 7.10 (s, 1H), 4.62-4.42 (m, 2H), 3.99-3.81 (m, 1H), 3.27-3.16 (m, 2H), 2.99 (s, 2H), 2.97-2.84 (m, 2H), 2.72 (s, 3H), 2.71 (s, 3H), 2.58-2.53 (m, 1H), 2.47-2.32 (m, 4H), 2.27-2.13 (m, 2H), 2.01-1.90 (m, 2H).

Example 2: Modification of a Small Molecule with Different Nucleophilic Groups

Materials and Methods 1,5-dansyl-L-lysine was synthesized as described in Hohsaka, et al. FEBS Letters. 2004. 560 (1-3), 173-177. Fmoc-1,5-dansyl-L-lysine was synthesized by dissolving 1,5 dansyl-L-lysine (3.7 mmol, 1 eq.) and Fmoc-Osu (Simga Aldrich Inc, 46920, 3.7 mmol, 1 eq.) in anhydrous acetone (20 mL) under argon atmosphere. DIPEA (2 eq.) was then added dropwise over 10 minutes. The solution was mixed for 20 hours. The reaction mixture was then diluted with ethyl acetate and washed with 5% $NaSO_4$, then with aqueous saturated NaCl solution. The organic phase was dried over $NaSO_4$, filtered and concentrated under reduced pressure. The residue was then purified by flash chromatography on silica (dichloromethane/methanol/acetic acid (89:10:1) to yield the Fmoc protected 1,5-dansyl-L-lysine as a yellow oil (944 mg, 42.5% over 2 steps). $^{1}H$ NMR (400 MHz, $(CD_3)_2SO$) δ (ppm=8.46 (d, J=8.5 Hz, 1H), 8.32 (d, J=8.6 Hz, 1H), 8.10 (d, J=7.2 Hz, 1H), 7.90-7.87 (m, 2H), 7.77-7.69 (m, 2H), 7.67-7.49 (m, 3H), 7.46-7.38 (m, 2H), 7.34-7.26 (m, 3H), 4.30-4.18 (m, 4H), 3.84-3.73 (m, 1H), 2.85 (s, 6H), 2.81-2.68 (m, 2H), 1.57-1.39 (m, 2H), 1.35-1.16 (m, 4H).

Sieber amide resin (Novabiochem, Cat 8550080025, Lot 56587608 721, 0.62 mmol/g, 1 eq., 0.673 mmol) was swelled in anhydrous DMF (10 mL) in a reaction syringe (Supelco, Cat #57118-U) for 30 minutes. DMF was removed under reduced pressure. The resin was deprotected by stirring with 20% v/v piperidine/DMF for 20 minutes. This was repeated. The resin was then washed three times with DMF. While the resin was being deprotected, Fmoc-1,5-dansyl-L-lysine (0.2 eq.) and HATU (0.2 eq.) were stirred in anhydrous DMF (2 mL) at room temperature for 30 minutes in a separate flask. The resin was reswelled in anhydrous DMF (10 mL). Fmoc-1,5-dansyl-L-lysine and HATU solution were added to the resin. DIPEA (0.4 eq.) was then added to the solution and was allowed to stir for 3 hours at room temperature. The resin was then washed three times with DMF. Unreacted sites on the resin were quenched by adding a solution of 5% acetic anhydride and 10% triethylamine in DMF (7 mL) for 30 min. The resin was then washed three times with DMF, three times with methanol, and then dried under reduced pressure. A test cleavage was performed, where a few beads of resin were collected, resuspended in 5% TFA in DCM, placed on a shaker for 30 min, then filtered through cotton and analyzed via LCMS. To assess resin loading, ten milligrams of resin was weighed out and set aside for quantification. The resin was then reswelled in anhydrous DMF (10 mL) for 30 minutes. Fmoc-1,5-dansyl-L-lysine was deprotected by adding 20% v/v piperidine/DMF for 20 minutes. This was repeated. A solution of succinic anhydride (0.6 eq.) and DIPEA (0.4 eq.) in DMF was added to the resin for 1.5 hours. The resin was then washed three times with DMF, three times with methanol, and then dried under reduced pressure. A test cleavage performed. To test the reactivity of the method with various nucleophiles, resin (~100 milligrams, 1 eq.) was added to 12 reaction syringes (Supelco, Cat #54222). The resin was then reswelled with anhydrous toluene (4 ml) under argon atmosphere for 30 minutes. Triethylamine (1 eq.) and DPPA (1 eq.) were added to each of the resin at room temperature for two hours. 4-ethylpyridine, 4-(aminomethyl) pyridine, benzyl mercaptan, 4-(methoxymethyl)pyridine, piperidine, aniline, R-(+)-alpha-methyl-4-pyiridinemethanol, 4-pyridylacetic acid hydrochloride, 4-pyridinemethanol, 2-(4-pyridiyl)-2-propanol, phenol, or indole (0.24 eq.) were added to the solution of a tube for 20 hours at 75° C. The resin was then quenched with anhydrous methanol (1 mL) for 10 minutes, then washed 3 times with methanol. The resin was cleaved with 5% TFA in DCM for 18 hours, filtered through cotton, and analyzed with LCMS. The loading of the beads was estimated using standard protocols (aaptec technical bulletin 1198). Dansyl chloride was added to the LCMS samples as an internal standard to quantify reaction efficiency based on resin loading.

Results

The functionalization of succinic anhydride modified dansyl-L-lysine with 4-(aminomethyl)pyridine was confirmed by LMCS (MW 583.71, retention time: 3.31, yield 67%). The observed mass corresponds to a demethylation of the product, which is commonly observed with our LCMS, as the ionization energy of the applied ESI is high.

The functionalization of succinic anhydride modified dansyl-L-lysine with benzyl mercaptan was confirmed by LMCS (MW 599.77, retention time: 4.307, yield 37%).

The functionalization of succinic anhydride modified dansyl-L-lysine with piperidine was confirmed by LMCS (MW 560.71, retention time: 3.956, yield 66%). The observed mass corresponds to a demethylation of the product, which is commonly observed with our LCMS, as the ionization energy of the applied ESI is high.

The functionalization of succinic anhydride modified dansyl-L-lysine with aniline was confirmed by LMCS (MW 568.69, retention time: 4.073, yield 37%).

The functionalization of succinic anhydride modified dansyl-L-lysine with phenol was confirmed by LMCS (MW 569.68, retention time: 4.076, yield 21%).

4-ethylpyridine, 4-(methoxymethyl)pyridine, and 4-pyridylacetic acid hydrochloride were chosen as negative controls due to their poor nucleophilicities and did not result in any conversion.

No product was observed for functionalization of succinic anhydride modified dansyl-L-lysine with R-(+)-alpha-methyl-4-pyiridinemethanol, 4-pyridinemethanol, 2-(4-pyridyl)-2-propanol, or indole. However, as discussed above, it is believed that the nucleophilicities of R-(+)-alpha-methyl-4-pyiridinemethanol, 4-pyridinemethanol, 2-(4-pyridyl)-2-propanol, and indole by either (i) activating the alcohols with 2 mole percent DMAP in toluene at 80° C. for 1 hour before adding the solution to the isocyanate functionalized group of interest (dansyl), (ii) mixing the isocyanate functionalized group of interest (dansyl) with dibutyltin(II)-dilaurate (0.02 equivalents (eq.)) and the alcohol (2 equivalents) in toluene at 60° C. for 48 hours, (iii) mixing the isocyanate functionalized group of interest (dansyl, 1.1 eq.) with the alcohol (1 eq.), CuCl (0.1 eq), and pyridine (10 eq.) in toluene at 50° C. for 2 hours, or iv) stirring the indole (1 eq.) with NaH (60% dispersion in mineral oil, 2 eq.) in DMF at 0° C. for 1 hour and then adding the mixture to the isocyanate functionalized group, as in published studies (Valois-Escamilla, I; Alvarez-Hernandez, A; Rangel-Ramos, LF; Suárez-Castillo, O R; Ayala-Mata, F; Zepeda-Vallejo, G; *Tetrahedron Lett.* 2011, 52(29), 3726-3728; Sandmann, B.; Happ, B; Hager, MD; Vitz, J; Rettler, E; Burtscher, P; Moszner, N; Schubert, US. *Journal of Polymer Science, Part A: Polymer Chemistry* 2014, 52, 239-247; Amada, H, Sekiguchi, Y, Ono, N, Koami, T, Takayama, T, Yabuuchi, T, Katakai, H, Ikeda, A, Aoki, M, Naruse, T, Wada, R, Nozoe, A, Sato, M. *Bioorg. Med. Chem.* 2012, 20(24), 7128-7138; Bhat, A. H, Alavi, S, Grove, H. K, *Org. Lett.* 2020, 22, 224-229.

Example 3: Modification of AP1497, an FKBP12 Binder, with a Photoactivatable Group and "Click" Handle

Materials and Methods

Fmoc-pANA-OH was synthesized as described below.

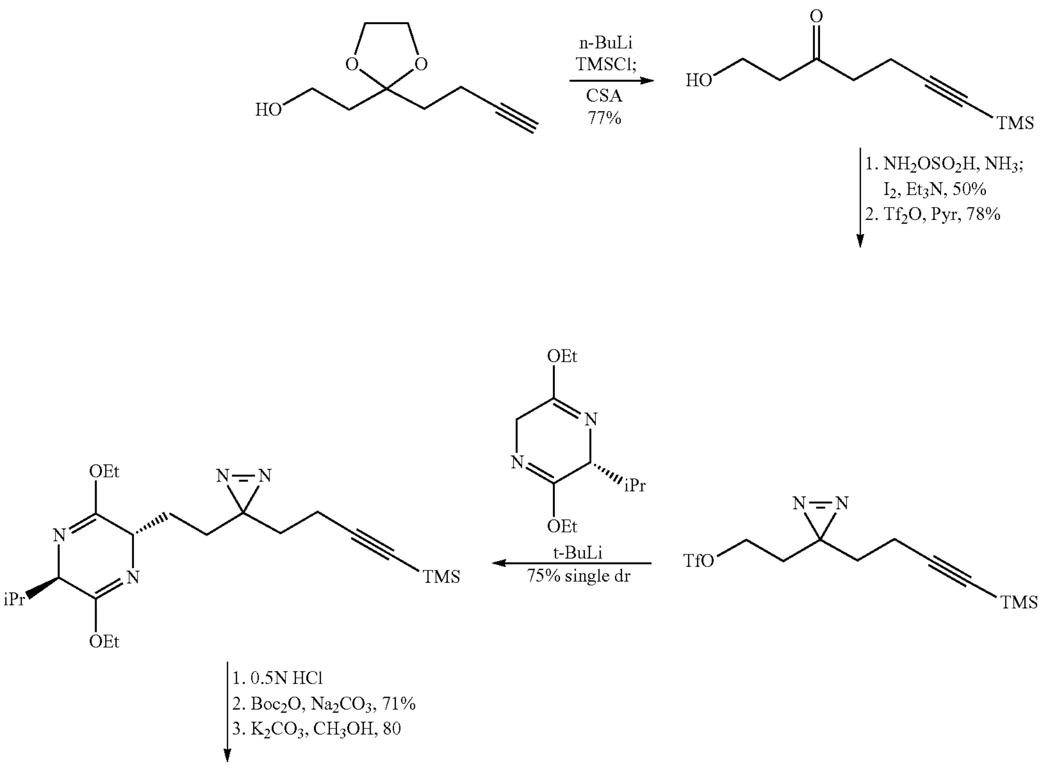

-continued

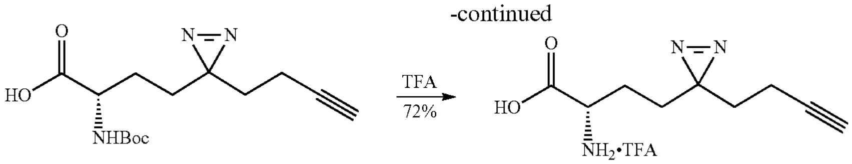

pANA•TFA

Synthesis of 1-hydroxy-7-(trimethylsilyl)hept-6-yn-3-one (2)

n-Butyl lithium (1.71 mL, 4.01 mmol, 2.20 eq.) was added to a stirred solution of the ketal 1 (252 mg, 1.84 mmol, 1.00 eq.) in tetrahydrofuran (5.2 mL) at −78° C. The reaction mixture was stirred continuously for 1 hour at −78° C. Trimethylsilyl chloride (694 μl, 5.47 mmol, 3.00 eq.) was added dropwise to the reaction mixture at −78° C. The reaction mixture was warmed to 24° C. and stirred for 2 hours at 24° C. The reaction was quenched by addition of an aqueous hydrochloric acid solution (2.0 M, 10 mL). The resulting biphasic mixture was transferred to a separatory funnel. The aqueous layer was extracted with ether (3×10 mL) and the organic layers were combined. The combined organic layers were transferred back to the separatory funnel and washed with a saturated solution of aqueous sodium bicarbonate (2×20 mL). The washed organic layer was dried over anhydrous sodium sulfate and filtered through a plug of cotton. The filtrate was concentrated under reduced pressure. The crude product was used in the next step without further purification.

Camphor sulfonic acid (22.0 mg, 95.0 μmol, 0.05 eq.) was added to a stirred solution of the crude product in a 40:1 mixture of acetonitrile-water (4.0 mL). The reaction mixture was stirred for 12 hours at 24° C. The resulting mixture was filtered through a plug of solid sodium bicarbonate (5 g). The filtrate was concentrated under reduced pressure to afford a yellow solid. The crude solid was purified by column chromatography ($SiO_2$, 20% ethyl acetate-hexanes) to provide the ketone 2 as a yellow oil (180 mg, 77% yield). $R_f$=0.15 (25% ethyl acetate-hexanes, ninhydrin). $^1H$ NMR (500 MHz, $CDCl_3$): δ 3.82 (t, J=5.0 Hz, 2H, $H_1$), 2.46 (t, J=7.0 Hz, 2H, H5), 2.73-2.63 (m, 4H, $H_2$ and $H_4$), 0.10 (s, 9H, TMS). $^{13}C$ NMR (125 MHz, $CDCl_3$): δ 209.1, 105.3, 85.3, 57.6, 44.7, 42.0, 14.3, 0.0. IR (ATR-FTIR), $cm^{-1}$: 3401.6 (brs), 2958.5 (w), 2898.9 (w), 2175.9 (m), 1711.2 (s), 1407.2 (m), 1368.5 (m), 1248.0 (s). HRMS-ESI (m/z): $[M+H]^+$ calculated for $C_{10}H_{98}O_2Si$, 199.1149; found 199.1150.

Synthesis of 2-(3-(4-(trimethylsilyl)but-3-yn-1-yl)-3H-diazirin-3-yl)ethan-1-ol (S1)

Ammonia (10-15 mL) was condensed in a flask containing a stirred solution of the ketone 2 (177 mg, 891 μmol, 1.00 eq.) in a 1:1 mixture of ether-methanol (1.0 mL) at −78° C. The reaction flask was kept under a constant positive pressure of nitrogen through a Schlenck line connected to a bubbler. The reaction mixture was allowed to warm to −20° C. and stirred for 2 hour at −20° C. The reaction mixture was cooled to −78° C. A solution of hydroxylamine-o-sulfonic acid (151 mg, 1.34 mmol, 1.50 eq.) in anhydrous methanol (500 μL) was added dropwise to the cooled mixture at −78° C. The reaction flask was covered with an excess of dry ice, wrapped in aluminum foil, and allowed to warm over 24 hours to 24° C. The warmed reaction mixture was stirred for 24 hours at 24° C. The resulting white paste was further dried under reduced pressure for 30 min at 24° C. The dried solid was taken up in dichloromethane (4.0 mL) and stirred for 5 min at 24° C. The resulting mixture was filtered through a plug of celite using a Büchner funnel. The filtrate was concentrated under reduced pressure to afford the crude product as a colorless oil.

The crude colorless oil was dissolved in dichloromethane (4.0 mL) and cooled to −4° C. Triethylamine (248 μL, 1.78 mmol, 2.00 eq.) was added to the stirred solution at −4° C. A solution of iodine (226 μg, 891 μmol, 1.00 eq.) in dichloromethane (4.0 mL) was added dropwise to the reaction mixture at −4° C. until the solution turned to a persistent orange-red color, indicative of the reaction completion. The reaction mixture was quenched by addition of aqueous sodium thiosulfate solution (30 mL) at −4° C. and allowed to warm to 24° C. The reaction mixture was stirred vigorously for 30 min at 24° C. or until the mixture turned colorless. The reaction mixture was transferred to a separatory funnel, and the resulting layers were separated. The aqueous layer was extracted with dichloromethane (2×20 mL) and the organic layers were combined. The combined organic layers were dried over anhydrous sodium sulfate. The dried organic layers were filtered, and the filtrate was concentrated under reduced pressure to afford the crude product as a colorless oil. The crude product was purified by column chromatography ($SiO_2$, 10% ethyl acetate-hexanes) to afford the diazirine S1 as a colorless oil (94.0 mg, 50% yield).

$R_f$=0.25 (25% ethyl acetate-hexanes, anisaldehyde). $^1H$ NMR (500 MHz, $CDCl_3$): δ 3.48 (t, J=5.0 Hz, 2H, $H_1$), 2.07 (t, J=5.5 Hz, 2H, $H_5$), 1.95 (brs, 1H, OH), 1.68 (t, J=5.5 Hz, 2H, $H_4$), 1.64 (t, J=5.0 Hz, 2H, $H_2$). $^{13}C$ NMR (125 MHz, $CDCl_3$): δ 105.6, 85.6, 57.3, 35.6, 32.8, 26.6, 14.5, 0.0. IR (ATR-FTIR), $cm^{-1}$: 3352.1 (brs), 2957.6 (m), 2918.9 (m) 2855 (m), 2177.0 (m), 1585.4 (w), 1445.4 (w), 1248.7 (s). HRMS-ESI (m/z): $[M-H]^-$ calculated for $C_{10}H_{17}N_2O_1Si$, 209.1116; found 209.1110.

Synthesis of 2-(3-(4-(trirnethylsilyl)but-3-yn-1-yl)-3H-diazirin-3-yl)ethyl trifluoromethanesulfonate (3)

Anhydrous pyridine (26.0 μL, 322 μmol, 1.00 eq.) and freshly distilled triflic anhydride (54.0 μL, 322 μmol, 1.00 eq.) were added to a stirred solution of the diazirine S1 (67.7 mg, 322 μmol, 1.00 eq.) in anhydrous dichloromethane (2.0 mL) at 0° C. The resulting mixture was stirred for 30 min at 0° C. The product mixture was quenched by addition of water (5.0 mL) and the biphasic solution was transferred to a separatory funnel. The layers that formed were separated, and the aqueous layer was extracted with dichloromethane (2×5 mL). The organic layers were combined and dried over anhydrous sodium sulfate. The dried solution was filtered, and the filtrate was concentrated under reduced pressure to afford the crude product as a pale yellow oil. The crude product was purified by column chromatography (Si02, 2% ethyl acetate-hexanes) to afford the triflate 3 as a colorless oil (86.0 mg, 78% yield). $R_f$=0.95 (5% ethyl acetate-hexanes, anisaldehyde). $^1$H NMR (400 MHz, $CDCl_3$): δ 4.40 (t, J=8.0 Hz, 2H, $H_1$), 2.10 (t, J=8.5 Hz, 2H, H5), 1.98 (t, J=8.5 Hz, 2H, $H_2$), 1.65 (t, J=8.5 Hz, 2H, $H_4$), 0.15 (s, 9H, TMS). $^{13}$C NMR (100 MHz, $CDCl_3$): δ 118.5 (q, J=318.4 Hz, CF3), 104.7, 86.2, 71.3, 33.3, 32.3, 25.3, 14.5, −0.14. IR (ATR-FTIR), $cm^{-1}$: 2961.4 (w), 2926.2 (w), 2859.7 (w), 2178.4 (w), 1589.2 (w), 1413.4 (s), 1246.1 (s), 1201.5 (s), 1142.2 (s), 949.5 (s), 921.1 (s), 838.8 (s). HRMS-ESI (m/z): $[M+H]^+$ calculated for $C_{11}H_{18}F_3N_2O_3SSi$, 343.0760; found 343.0760.

Synthesis of (2R,5S)-3,6-diethoxy-2-isopropyl-5-(2-(3-(4-(trimethylsilyl)but-3-yn-1-yl)-3H-diazirin-3-yl)ethyl)-2,5-dihydropyrazine (5)

t-Butyl lithium (1.7 M in tetrahydrofuran, 110 μL, 190 μmol, 1.00 eq.) was added to a stirred solution of the bislactam 4 (35.0 mg, 190 μmol, 1.00 eq.) in anhydrous tetrahydrofuran (750 μL) at −78° C. The reaction mixture was stirred for 1 hour at −78° C. A solution of the triflate 3 (65.0 mg, 190 μmol, 1.00 eq.) in tetrahydrofuran (100 μL) was added dropwise to the stirred reaction mixture at −78° C. The resulting mixture was warmed over 90 minutes to 24° C. and stirred continuously for 8 hours at 24° C. The product mixture was quenched by addition of a saturated aqueous ammonium chloride solution (2.0 mL) and water (2.0 mL). The biphasic solution was transferred to a separatory funnel. The resulting layers were separated, and the aqueous layer was extracted with ether (2×5 mL). The organic layers were combined and dried over anhydrous sodium sulfate. The dried solution was filtered, and the filtrate was concentrated under reduced pressure. The crude product was purified by column chromatography ($SiO_2$, 0.5% ethyl acetate-hexanes) to afford the dihydropyrazine 5 as a colorless oil (58.0 mg, 75% yield). $R_f$=0.89 (5% ethyl acetate-hexanes, anisaldehyde). $^1$H NMR (400 MHz, $CDCl_3$): δ 4.20-4.03 (m, 4H, $H_{10}$ and $H_{12}$), 3.91 (m, 1H, $H_6$), 3.88 (m, 1H, $H_3$), 2.24 (m, 1H, $H_7$), 2.04 (t, J=8.0 Hz, 2H, $H_{18}$), 1.70 (m, 1H, $H_{14a}$), 1.61 (t, J=7.5 Hz, 2H, $H_{15}$), 1.55 (m, 1H, $H_{14b}$), 1.35 (t, J=8.0 Hz, 2H, $H_{17}$), 1.30-1.24 (m, 6H, $H_{11}$ and $H_{13}$), 1.01 (d, J=7.0 Hz, 3H, $H_9$), 0.70 (d, J=7.0 Hz, 3H, $H_8$), 0.14 (s, 9H, TMS). $^{13}$C NMR (100 MHz, $CDCl_3$): δ 163.3, 162.6, 105.5, 85.3, 60.8, 60.6, 60.5, 54.4, 32.6, 32.0, 28.3, 28.2, 28.1, 19.0, 16.7, 14.7, 14.3, 14.3, 0.0. IR (ATR-FTIR) $cm^{-1}$: 2990 (s), 2985 (s), 2960 (s), 2100 (m), 1745 (s). HRMS-ESI (m/z): $[M+H]^+$ calculated for $C_{21}H_{37}N_4O_2Si$, 405.2686; found 405.2686.

Synthesis of ethyl (S)-2-((tert-butoxycarbonyl)amino)-4-(3-(4-(trimethylsilyl)but-3-yn-1-yl)-3H-diazirin-3-yl)butanoate (6)

Hydrochloric acid (0.5 M in water, 6.0 mL) was added to a stirred solution of the dihydropyrazine 5 (489 mg, 1.47 mmol, 1.00 eq.) in acetonitrile (6.0 mL) at 0° C. The reaction mixture was warmed to 24° C. and stirred for 8 hours at 24° C. The product mixture was concentrated under reduced pressure and the residue obtained was dissolved in water (20 mL). The aqueous solution was basified to pH 14.0 by a 50% aqueous ammonium hydroxide solution. The basified solution was transferred to a separatory funnel and extracted with ethyl acetate (2×20 mL). The organic layers were combined and dried over anhydrous sodium sulfate. The dried solution was filtered, and the filtrate was concentrated under reduced pressure to afford the crude amine product as pale yellow solid. The crude product was used in the next step without further purification.

Di-tert-butyl dicarbonate (706 mg, 3.23 mmol, 2.20 eq.) was added to a stirred solution of the crude product in tetrahydrofuran (6.0 mL) and the mixture was stirred continuously for 8 hours at 24° C. The product mixture was transferred to a separatory funnel containing a 1:1 mixture of ether-water (40 mL). The layers were mixed and separated. The aqueous layer was extracted with ether (2×10 mL). The organic layers were combined and dried over anhydrous sodium sulfate. The dried solution was filtered, and the filtrate was concentrated under reduced pressure to afford the crude product as a colorless oil. The crude product was purified by column chromatography ($SiO_2$, 10% ethyl acetate-hexanes) to afford the ester 6 as viscous oil (412 mg, 71% yield). $R_f$=0.10 (10% ethyl acetate-hexanes, anisaldehyde). $^1$H NMR (500 MHz, $CDCl_3$): δ 5.03 (bs, 1H, $H_{13}$), 4.16 (m, 1H, $H_2$), 4.15 (q, J=7.50 Hz, 2H, $H_{11}$), 1.99 (t, J=7.40 Hz, 2H, $H_7$), 1.63 (m, 1H, $H_{3a}$), 1.57 (t, J=6.80 Hz, 2H, $H_4$), 1.48 (m, 1H, $H_{3b}$), 1.40 (s, 9H, t-Bu), 1.24 (t, J=7.60 Hz, 2H, $H_6$), 0.11 (s, 9H, TMS). $^{13}$C NMR (100 MHz, $CDCl_3$): δ 172.1, 155.3, 105.2, 85.5, 79.9, 61.4, 52.8, 32.4, 28.9, 28.2, 27.0, 14.6, 14.1, −0.05. IR (ATR-FTIR), $cm^{-1}$: 3300.00 (brs), 3296.96 (brs), 2979.3 (m), 2929.5 (m), 1712.24 (s), 1508.5 (m), 1453.3 (m), 1392.5 (m), 1097.7 (s). HRMS-ESI (m/z): $[M+Na]^+$ calculated for $C_{19}H_{33}N_3O_4SiNa$, 418.2138; found 418.2138.

Synthesis of (S)-4-(3-(but-3-yn-1-yl)-3H-diazirin-3-yl)-2-((tert-butoxycarbonyl)amino)butanoic acid (Boc-pANA-OH)

Potassium carbonate (4.44 g, 32.1 mmol, 3.00 eq.) was added to a stirred solution of the ester 6 (422 mg, 10.7 mmol, 1.00 eq.) in ethanol (10 mL) at 24° C., and the mixture was stirred continuously for 8 hours at 24° C. The product mixture was cooled to 0° C., and water (10 mL) was added. The reaction mixture was allowed to warm to 24° C., and the warmed mixture was stirred for 8 hours at 24° C. The product mixture was concentrated under reduced pressure, and the resulting aqueous solution was transferred to a separatory funnel charged with water (30 mL) and ether (30 mL). The layers were mixed and the organic layer was separated and discarded. The remaining aqueous layer was collected in an Erlenmeyer flask (100 mL), and cooled to 0° C. An aqueous solution of sodium bisulfite (3 M) was slowly added to the cooled solution until a white and murky suspension emerged (~15 mL). The product mixture was transferred to a separatory funnel containing ether (50 mL). The layers were mixed and the organic layer was collected. The aqueous layer was extracted with ether (2×50 mL). The organic layers were combined and dried over anhydrous sodium sulfate. The resulting mixture was filtered, and the resulting filtrate was concentrated under reduced pressure. The residue obtained was subjected to column chromatography ($SiO_2$, 10% ethyl acetate-hexanes) to afford the acid Boc-pANA-OH as colorless oil (2.53 g, 80% yield).

$R_f$=0.10 (90% ethyl acetate-hexanes, anisaldehyde). $^1$H NMR (500 MHz, $CD_3CN$): δ 7.74 (brs, 1H, COOH), 5.61 (brs, 1H, $H_{10}$), 4.06 (brs, 1H, $H_2$), 2.23 (t, J=2.62 Hz, 1H, $H_9$), 2.05 (td, J=7.45, 2.62 Hz, 2H, $H_7$), 1.64 (t, J=7.55 Hz, 2H, $H_6$), 1.52 (t, J=8.90 Hz, 2H, $H_4$), 1.56-1.44 (m, 2H, $H_3$). 1.44 (s, 9H, t-Bu). $^{13}$C NMR (125 MHz, $CD_3CN$): δ 173.3, 155.8, 83.0, 79.2, 69.5, 52.7, 31.8, 28.7, 27.9, 27.6, 25.5, 12.8. IR (ATR-FTIR), $cm^{-1}$: 3390.3 (brs), 3300.6 (brs), 3111.3 (brs), 2979.8 (m), 2928.4 (m), 1714.5 (s), 1512.9 (m), 1453.7 (m), 1252.2 (m), 1163.2 (s). HRMS-ESI (m/z): $[M-H]^-$ calculated for $C_{14}H_{20}N_3O_4$, 294.1459; found 294.1460.

Synthesis of (S)-2-amino-4-(3-(but-3-yn-1-yl)-3H-diazirin-3-yl)butanoic acid trifluoro acetic acid salt (pANA)

Trifluoroacetic acid (1.5 mL) was added to a stirred solution of the acid Boc-pANA-OH (411 mg, 1.39 mmol, 1.00 eq.) in dichloromethane (15 mL) at 0° C. The mixture was stirred for 2 hours at 24° C. The product mixture was concentrated under reduced pressure and dried azeotropically with toluene. The crude product was purified by trituration using ether at −78° C. to 0° C. to provide the TFA salt pANA as a white solid (387 mg, 90% yield). $^1H$ NMR (500 MHz, $D_2O$): δ 3.56 (dd, J=6.0, 6.0 Hz, 1H, $H_2$), 2.28 (m, 1H, $H_9$), 1.95 (m, 2H, $H_7$), 1.68-1.38 (m, 6H, H3, $H_4$, and $H_6$). $^{13}C$ NMR (125 MHz, $D_2O$): δ 174.0, 84.3, 69.8, 54.0, 30.7, 28.4, 27.9, 24.8, 12.4. IR (ATR-FTIR), $cm^{-1}$: 3460.8 (brs, COOH), 3287.9 (brs, COOH), 3058.0 (brs, COOH), 2949.7 (m), 2921.8 (m), 2852.4 (m), 1581.0 (s), 1513.0 (s), 1327.8 (m). HRMS-ESI (m/z): $[M+H]^+$ calculated for $C_9H_{15}N_3O_2$, 196.1081; found 196.1081.

Synthesis of (S)-2-((((9H-fluoren-9-yl)methoxy)carbonyl)amino)-4-(3-(but-3-yn-1-yl)-3H-diazirin-3-yl)butanoic acid (Fmoc-pANA-OH)

Fmoc-OSu (590 mg, 1.75 mmol, 1.20 eq.) and 10% aqueous sodium carbonate (5 mL) was added to a solution of pANA (450 mg, 1.46 mmol, 1.00 eq.) in acetone (5 mL) at 24° C. The resulting mixture was stirred overnight at 24° C. The reaction mixture was concentrated under reduced pressure and the resulting solid was taken up in a mixture of ethyl acetate (20 mL) and water (20 mL). The mixture was poured into a separatory funnel, and the layers were separated. The aqueous layer was extracted with ethyl acetate (2×10 mL). The organic layers were combined and dried over anhydrous sodium sulfate. The dried solution was filtered through a plug of cotton, and the filtrate was concentrated under reduced pressure. The crude product was purified by column chromatography ($SiO_2$, 50% ethyl acetate-hexanes) to afford Fmoc-pANA-OH (548 mg, 90%). $R_f$=0.23 (50% ethyl acetate-hexanes, ninhydrin). $^1H$ NMR (500 MHz, $CD_3CN$): 11.0 (brs, 1H, COOH), 7.95-7.30 (m, 8H, ArH;Fmoc), 6.00 (brs, 1H, NH), 4.44-4.33 (m, 2H, $H_{11}$), 4.27 (dd, J=6.5 Hz, 1H, H12), 4.11 (m, 1H, $H_2$), 2.23 (t, J=2.0 Hz, 1H, $H_9$), 2.05 (td, J=6.9, 2.0 Hz, 2H, $H_7$), 1.65 (t, J=6.5 Hz, 2H, $H_4$), 1.52 (t, J=6.9 Hz, 2H, $H_6$), 1.74-1.62 and 1.58-1.48 (m, 2H, $H_3$). $^{13}C$ NMR (125 MHz, $CDCl_3$): 173.7, 147.2, 145.1 and 145.2, 142.2, 128.8, 128.2, 126.2, 120.0, 83.0. 69.4, 66.4, 53.2, 47.1, 32.7, 29.8, 28.9, 26.5, 13.8. 2-(3-(3-(3,4-dimethoxyphenyl)-1-((1-(3,3-dimethyl-2-oxopentanoyl)piperidine-2-carbonyl)oxy)propyl)phenoxy)acetic acid (AP1497) was synthesized as described in Ong et al. PNAS. 106 (12). 4617-4622.

Synthesis of 1-(3-(2-((2-arninoethyl)arnino)-2-oxoethoxy)phenyl)-3-(3,4-dimethoxyphenyl)propyl 1-(3,3-dimethyl-2-oxopentanoyl)piperidine-2-carboxylate (AP1497-amine)

AP1497 (100 mg, 1.2 eq.) and HATU (1.2 eq.) were dissolved in anhydrous DMF (5 mL) under an argon atmosphere. N-Boc-ethylenediamine (Sigma Aldrich, Cat #15369, 1 eq.) and DIPEA (2 eq.) were added to the solution and stirred for 4 hours at room temperature. The solution was diluted with water and extracted with ethyl acetate. The organic layer was washed with saturated NaCl, dried over sodium sulfate, and concentrated. The amine was then purified with HPLC to afford a clear oil (24 mg, 24% yield). $^1H$ NMR (500 MHz, $(CD_3)_2SO$) δ (ppm)=8.08-7.99 (m, 1H), 7.35-7.26 (m, 1H), 7.01-6.88 (m, 3H), 6.87-6.83 (m, 1H), 6.82-6.74 (m, 1H), 6.73-6.65 (m, 1H), 5.73-5.66 (m, 1H), 5.16 (d, J=5.3 Hz, 1H), 4.50-4.42 (m, 2H), 3.72 (d, J=7.7 Hz, 6H), 3.17-2.98 (m, 4H), 2.61-2.55 (m, 3H), 2.28-2.03 (m, 3H), 1.76-1.54 (m, 6H), 1.30-1.05 (m, 10H), 0.84-0.75 (m, 3H).

Sieber amide resin (Novabiochem, Cat 8550080025, 0.62 mmol/g, 1 eq., 0.673 mmol) was swelled in anhydrous DMF (4 mL) in a reaction syringe (Supelco, Cat #54222) for 30 minutes. DMF was removed. The resin was deprotected by stirring with 20% v/v piperidine/DMF for 20 minutes. This was repeated. The resin was then washed three times with DMF. While the resin was being deprotected, Fmoc-pANA-OH (0.2 eq.) and HATU (0.2 eq.) were stirred in anhydrous DMF (2 mL) at room temperature for 30 minutes in a separate flask. The resin was reswelled in anhydrous DMF (2 mL). The Fmoc-pANA-OH and HATU solution was added to the resin. DIPEA (0.4 eq.) was then added to the solution and was allowed to stir for 3 hours at room temperature. The resin was then washed three times with DMF. Unreacted sites on the resin were quenched by adding a solution of 5% acetic anhydride and 10% triethylamine in DMF (7 mL) for 30 min. The resin was then washed three times with DMF, three times with methanol, and then dried under reduced pressure. A test cleavage was performed, where a few beads of resin were collected, resuspended in 5% TFA in DCM, placed on a shaker for 30 min, then filtered through cotton and analyzed LCMS. To assess resin loading, ten milligrams of resin was weighed out and set aside for analysis. The resin was then reswelled in anhydrous DMF (4 mL) for 30 minutes. Fmoc-pANA-OH was deprotected by adding 20% v/v piperidine/DMF for 20 minutes. This was repeated. A solution of succinic anhydride (0.6 eq.) and DIPEA (0.4 eq.) in DMF was added to the resin for 1.5 hours. The resin was then washed three times with DMF, three times with methanol, and then dried under reduced pressure. A test cleavage was performed. The resin was then reswelled with anhydrous toluene (4 ml) for 30 minutes. Triethylamine (1 eq.) and DPPA (1 eq.) were added to the resin at room temperature for two hours. AP1497-amine (0.006 mmol, 0.086 eq.) was added to the resin and stirred for 20 hours at 75° C. The resin was then quenched with anhydrous methanol (1 mL) for 10 minutes, then washed 3 times with methanol. The resin was cleaved with 5% TFA in DCM for 18 hours, filtered through cotton, and analyzed with LCMS (FIG. 3). The loading of the beads was estimated using standard protocols (aaptec technical bulletin 1198).

Half the crude product was submitted for NMR with maleic acid as an internal standard to quantify reaction efficiency based on resin loading.

Half the crude product was dissolved in anhydrous DMF. Recombinant human FKBP12-His (7.6 mg/ml) and FKBP12-SNAP (5.6 mg/ml) were purified from *E. coli* and stored in 20 mM Tris-HC1, 100 mM NaCl, 1 mM DTT and 10% glycerol at −80° C. Recombinant human FKBP12-His and FKBP12-SNAP were individually diluted in HEPES Buffered Saline (150 mM NaCl, 50 mM HEPES, 1% IGEPAL CA-630 (Sigma Aldrich, Cat #18896), protease inhibitor mini tablet (Thermo Scientific, Cat #A32953)). Recombinant human FKBP12-His (1.5 uM) and FKBP12-

SNAP (1.7 uM) were each treated with the crude product (10 uM) for 1 hour at 4° C. Both samples were then split into two tubes. One tube was UV irradiated (~350 nm) on ice and the other tube was kept in the dark on ice. A copper mediated click chemistry kit (Invitrogen, Cat #C10643) was used to install Alexa Fluor 647 picolyl azide on the probe-labeled proteins. Excess fluorophore was removed as in established protocols (Click Chemistry Tools, Cell Lysate Labeling Protocol, downloaded Feb. 2, 2020). The samples were resuspended in 1% SDS in PBS and mixed with sample buffer (Bio-Rad, Cat #1610747).

The proteins (~0.03 nmol protein loaded per lane) were resolved using sodium dodecyl-sulfate polyacrylamide gel electrophoresis (SDS-PAGE, Bio-Rad, Cat #5671084) and transferred to nitrocellulose membrane. The membrane was blocked with 5% bovine serum albumin (BSA) in Tris-buffered saline (TBST, 50 mM Tris pH8, 150 mM NaCl) containing 0.1% Tween-20 for 1 hour. Anti-FKBP12 antibody (abcam2918, 1:2000) in 1% BSA in TBST was added to the membrane for 1 hour. The membrane was then washed with TBST, incubated with anti-rabbit secondary (LI-COR Biosciences, Cat #926-32211) for 1 hour, and washed with TBST. Proteins were visualized via fluorescence on a LI-COR Odyssey CLx.

Results

The functionalization of succinic anhydride modified pANA-OH was confirmed by LCMS (MW 917.07, retention time 4.806). The yield of the reaction is estimated be 3.4% based on the maleic acid internal standard. Recombinant human FKBP12-His and FKBP12-SNAP that were treated with compound and UV-irradiated were labeled with Alexa Fluor 647. In the absence of UV light, there was negligible protein labeling.

Example 4: Immobilizing an Alkyne-Containing Protein Complex on an Azide Functionalized Well Plate

Materials and Methods

Recombinant human FKBP12-SNAP (20 uM) was labeled with an alkyne (MedChemExpress, Cat #HY-23926, 30 uM) in PBS with 1 mM DTT for 1 hour at 37° C. Unreacted substrate was removed by dialysis (20 mM $NaH_2PO_4$, 150 mM NaCl, 1 mM DTT and 10% glycerol) and the alkyne labeled protein (0.448 mg/ml) was stored at −80° C.

6-azidomethylnicotinic acid was synthesized as previously described. Uttamapinant, et al. Angew. Chem. Int. Ed. 2012, 51, 5852-5856.

Synthesis of N-(23-amino-3,6,9,12,15,18,21-heptaoxatricosyl)-6-(azidomethyl)nicotinamide 6-azidomethylnicotinic acid (1 eq.) and HATU (1.2 eq.) were dissolved in anhydrous DMF under argon atmosphere. t-boc-N-amido-PEG7-amine (Broadpharm, Cat #BP-22320, 2 eq.) and DIPEA (2 eq.) were added to the solution and stirred for 18 hours at room temperature. The solution was diluted with water and extracted with ethyl acetate. The organic layer was washed with aqueous saturated NaCl solution, dried over sodium sulfate, and concentrated under reduced pressure. The product was then purified with HPLC to afford a clear oil. The Boc protecting group was cleaved off by stirring the Boc-protected azide with 30% TFA in DCM for 20 hours. The solvent was removed under reduced pressure and the resulting oil was analyzed by NMR (140 mg, 47% over 2 steps). $^1H$ NMR (500 MHz, $(CD_3)_2SO$) δ (ppm)=9.00 (s, 1H), 8.76 (t, J=5.4 Hz, 1H), 8.23 (dd, J=8.1, 1.9 Hz, 1H), 7.54 (d, J=8.1 Hz, 1H), 4.60 (s, 2H), 3.62-3.42 (m, 34H), 3.03-2.94 (m, 2H).

N-(23-amino-3,6,9,12,15,18,21-heptaoxatricosyl)-6-(azidomethyl)nicotinamide (25.3 mM in DMSO) was diluted in 100 mM sodium carbonate, pH 9.6 (1:1000). The solution (100 ul) was added to each well of an amine reactive 96 well plate (Life Sciences Technology Corporation DBA Invitrogen, Cat #436007) for 1 hour at room temperature. The wells were then washed 5× with phosphate buffered saline with 0.05% Tween 20 (PBST, 137 mM NaCl, 2.7 mM KCl, 10 mM $NaH_2PO_4$, 1.8 mM $KH_2PO_4$, 0.05% Tween 20 (w/v), pH 7.6) (200 uL). Unreacted amine reactive sites were then blocked with 10 mM ethanolamine in 100 mM sodium carbonate for 18 hours at 4° C. with gentle shaking. The wells were then washed 5× for 3 minutes with PBST (200 uL). FKBP12-SNAP-alkyne was immobilized to the plate using a copper mediated click chemistry kit (Thermo Fisher Scientific, Cat #C10643). The wells were washed 5× with PBST containing 2% SDS, washed 5× with PBST, and then incubated with streptactin-horseradish peroxidase (HRP) antibody (BioRad, Cat #1610381, 1:10,000) in PBST for 1 hour at room temperature with gentle agitation. The wells were then washed 5× for 3 minutes with PBST (200 uL). HRP substrate (Life Science Technologies Corporation DBA Invitrogen, Cat #37074, 100 ul) was added to the wells and chemiluminescence was imaged using a Tecan Infinite M200 Pro.

Results

Wells containing SNAP-FKBP12-alkyne had higher luminescent signal than negative control wells containing SNAP-FKBP12.

The methods, compounds, and compositions herein described and further illustrated in the examples, which are provided by way of illustration and are not intended to be limiting. Theoretical aspects are presented with the understanding that Applicant does not seek to be bound by the theory presented. All parts or amounts, unless otherwise specified, are by weight. Those skilled in the art will recognize, or be able to ascertain using no more than routine experimentation, many equivalents to the specific embodiments of the invention described herein. Such equivalents are intended to be encompassed by the following claims.

We claim:

1. A compound having a structure:

Formula III

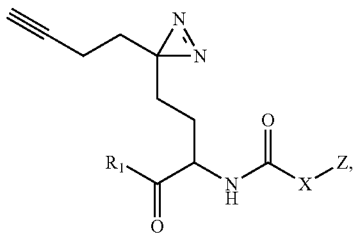

-continued

Formula IV

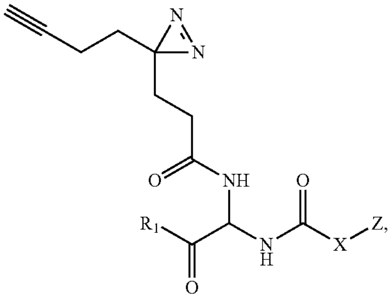

Formula V

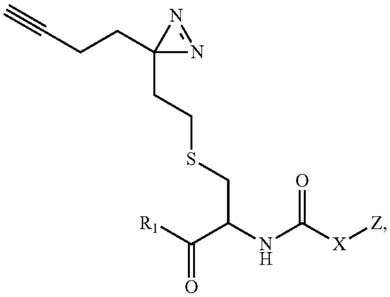

Formula X

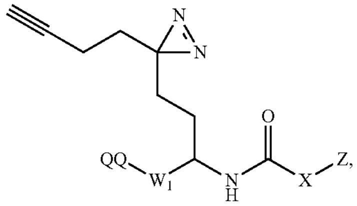

Formula XI

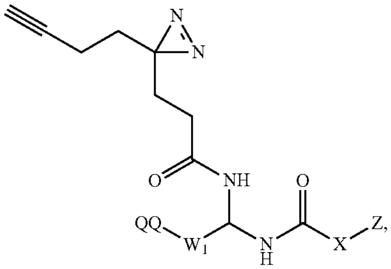

or

Formula XII

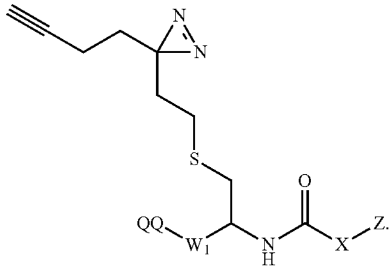

wherein:

when present $R_1$ is-OH or $NR_2R_3$, —$NR_2C(O)R_3$, $R_2$ and $R_3$ are independently hydrogen, unsubstituted alkyl, or substituted alkyl, Z is a small molecule moiety having a molecular weight less than 2,500 Da, X is O, NR', or S, QQ is absent, one or more resins, or well plates, wherein, when QQ is absent, $W_1$ comprises a carboxyl group, optionally-C(O) OH; a carbonyl group, optionally —$C(O)R_{1w}$); an ester, optionally —$C(O)OR_{1w}$ or —$OC(O)R_{1w}$; an amide optionally —$C(O)NR_{2w}R_{3w}$ or —$NR_{2w}C(O)R_{3w}$; a thioester, optionally —$C(O)SR_{4w}$ or —$SC(O)R_{4w}$; a hydrazide, optionally —C(O) $NHNH_2$; an amine; or a carbinol, optionally —$CH_2OH$, wherein, when QQ is present, $W_1$ comprises —OC(O)—, —C(O)O—, —$NR_{2w}C(O)$—, —$NR_{2w}$—, —C(O)—, —C(O)S—, —SC(O)—, —NHNHC(O)—, —S—, —O—, or a combination thereof wherein R', $R_{1w}$-$R_{4w}$ are independently hydrogen, unsubstituted alkyl, substituted alkyl, unsubstituted alkenyl, substituted alkenyl, unsubstituted alkynyl, substituted alkynyl, unsubstituted heteroalkyl, substituted heteroalkyl, unsubstituted cycloalkyl, substituted cycloalkyl, unsubstituted heterocyclyl, substituted heterocyclyl, substituted aryl, unsubstituted aryl, substituted heteroaryl, unsubstituted heteroaryl, substituted hydroxyamino, or unsubstituted hydroxyamino.

2. The compound of claim 1, wherein W1 comprises —C(O)OH, —$C(O)R_{1w}$, —$C(O)OR_{1w}$, —$OC(O)R_{1w}$, —$C(O)NR_{2w}R_{3w}$, —$NR_{2w}C(O)R_{3w}$, —$C(O)SR_{4w}$, —SC(O) $R_{4w}$, —$C(O)NHNH_2$, or —$CH_2OH$, wherein $R_{2w}$ and $R_{3w}$ independently hydrogen, unsubstituted alkyl, or substituted alkyl.

3. The compound of claim 1, wherein the one or more resins are selected from the group consisting of trityl resins, hydrazinobenzyol resins, Dawson Dbz AM resins, sulfonamide resins, HMBA resins, Merrifield resins, PAM resins, BHA resins, MBHA resins, Wang resins, brominated Wang resins, 4-nitrobenzophenone oxime resins, 4-(hydroxymethyl) phenoxyacetic acid resins, HMPB resins, Rink acid resins, Rink amide resins, PAL resins, Sieber amide resins, 4-sulfoamoylbenzoyl resins, aminoalkylated resins, hydroxyalkylated resins, brominated polystyrene resins, bromoalkylated resins, acrylamide-PEG copolymer resins, 4-(4-formyl-3-methoxyphenoxy) ethyl resins, melamine resins, acrylate resins, epoxy resins, urethane resins, silicone resins, fluoropolymer resins, and a combination thereof.

4. A collection of compounds comprising a plurality of the compounds of claim 1.

5. A method for the synthesis of the collection of compounds of claim 4, the method comprising:

(i) reacting one or more compounds with the surface of a resin or well plate to attach the one or more compounds to the resin or to the well plate via W1.

6. The method of claim 5, wherein the one or more compounds of step (i) comprise a carboxyl, a carbonyl, an amine, a hydroxyl, a thiol, a hydrazine, a hydroxylamine, an ester, a thioester, or a combination thereof.

7. The method of claim 5 further comprising:

(ii) reacting one or more additional compounds with at least one of the one or more compounds in step (i) attached on the surface of the resin or well plate to form —NHC(O)X—.

8. The method of claim 7, wherein reacting the one or more additional compounds of step (ii) to form —NHC(O) X— involves an isocyanate functional group.

9. The compound of claim 1, wherein Z has a molecular weight between 70 Da and 2,500 Da.

* * * * *